United States Patent
Heinrich et al.

(10) Patent No.: US 8,353,930 B2
(45) Date of Patent: *Jan. 15, 2013

(54) STRUCTURE FOR APPLYING SPRAYABLE WOUND TREATMENT MATERIAL

(75) Inventors: Russell Heinrich, Madison, CT (US); Michael J. Bettuchi, Middletown, CT (US); David Fowler, Cheshire, CT (US); Robert Capella, Shelton, CT (US); John Hauschild, Riverside, CT (US)

(73) Assignee: Covidien LP, Mansfield, MA (US)

( * ) Notice: Subject to any disclaimer, the term of this patent is extended or adjusted under 35 U.S.C. 154(b) by 146 days.

This patent is subject to a terminal disclaimer.

(21) Appl. No.: 12/909,161

(22) Filed: Oct. 21, 2010

(65) Prior Publication Data
US 2011/0036889 A1 Feb. 17, 2011

Related U.S. Application Data

(63) Continuation of application No. 11/250,277, filed on Oct. 14, 2005, now Pat. No. 7,922,743.

(60) Provisional application No. 60/620,102, filed on Oct. 18, 2004, provisional application No. 60/620,150, filed on Oct. 18, 2004.

(51) Int. Cl.
*A61B 17/04* (2006.01)
(52) U.S. Cl. ........... 606/219; 227/179.1; 227/178.1
(58) Field of Classification Search .... 227/175.1–182.1; 606/219
See application file for complete search history.

(56) References Cited

U.S. PATENT DOCUMENTS

| | | | |
|---|---|---|---|
| 3,079,606 A | 3/1963 | Bobrov et al. | |
| 3,490,675 A | 1/1970 | Green et al. | |
| 3,499,591 A | 3/1970 | Green | |
| 4,429,695 A | 2/1984 | Green | |
| 4,603,693 A * | 8/1986 | Conta et al. ............. | 227/179.1 |
| 4,873,977 A | 10/1989 | Avant et al. | |
| 5,065,929 A | 11/1991 | Schulze et al. | |
| 5,156,613 A | 10/1992 | Sawyer | |
| 5,156,614 A | 10/1992 | Green et al. | |
| 5,205,459 A * | 4/1993 | Brinkerhoff et al. ..... | 227/179.1 |
| 5,254,113 A | 10/1993 | Wilk | |
| 5,318,531 A | 6/1994 | Leone | |
| 5,392,979 A | 2/1995 | Green et al. | |
| 5,465,896 A | 11/1995 | Allen et al. | |
| 5,542,594 A | 8/1996 | McKean et al. | |

(Continued)

FOREIGN PATENT DOCUMENTS
EP 0 577 373 A2 1/1994
(Continued)

OTHER PUBLICATIONS

European Search Report for EP 05809831.0-1269 date of completion is May 4, 2012 (10 pages).

(Continued)

*Primary Examiner* — Darwin Erezo

(57) ABSTRACT

The present disclosure relates to surgical instruments, structures and methods for enhancing the properties of tissue to be repaired or joined. According to an aspect of the present disclosure, a surgical stapling apparatus is provided including a wound treatment material dispersion system for delivering wound treatment material to a target surgical site. The dispersion system includes an aperture formed in the anvil assembly oriented to dispense wound treatment material in an outward direction; and a source of wound treatment material in fluid communication with the aperture of the anvil assembly.

17 Claims, 24 Drawing Sheets

U.S. PATENT DOCUMENTS

| | | | |
|---|---|---|---|
| 5,554,119 | A | 9/1996 | Harrison et al. |
| 5,611,775 | A | 3/1997 | Machold et al. |
| 5,669,934 | A | 9/1997 | Sawyer |
| 5,690,675 | A | 11/1997 | Sawyer et al. |
| 5,735,833 | A | 4/1998 | Olson |
| 5,749,895 | A | 5/1998 | Sawyer et al. |
| 5,799,857 | A | 9/1998 | Robertson et al. |
| 5,824,015 | A | 10/1998 | Sawyer |
| 5,843,033 | A | 12/1998 | Ropiak |
| 5,866,561 | A | 2/1999 | Ungs |
| 5,895,412 | A | 4/1999 | Tucker |
| 5,915,616 | A | 6/1999 | Viola et al. |
| 5,931,165 | A | 8/1999 | Reich et al. |
| 5,964,394 | A | 10/1999 | Robertson |
| 6,032,849 | A | 3/2000 | Mastri et al. |
| 6,045,560 | A | 4/2000 | McKean et al. |
| 6,149,641 | A | 11/2000 | Ungs |
| 6,165,201 | A | 12/2000 | Sawhney |
| 6,179,862 | B1 | 1/2001 | Sawhney |
| 6,228,051 | B1 | 5/2001 | Trumbull |
| 6,287,323 | B1 | 9/2001 | Hammerslag |
| 6,398,797 | B2 | 6/2002 | Bombard et al. |
| 6,451,029 | B1 | 9/2002 | Yeatman |
| 6,488,197 | B1 * | 12/2002 | Whitman .................. 227/180.1 |
| 6,491,201 | B1 * | 12/2002 | Whitman .................. 227/180.1 |
| 6,623,452 | B2 | 9/2003 | Chien et al. |
| 6,681,979 | B2 * | 1/2004 | Whitman .................. 227/180.1 |
| 6,695,199 | B2 * | 2/2004 | Whitman .................. 227/180.1 |
| 7,141,055 | B2 * | 11/2006 | Abrams et al. ................. 606/115 |
| 7,238,195 | B2 * | 7/2007 | Viola ............................ 606/219 |
| 7,455,682 | B2 * | 11/2008 | Viola ............................ 606/219 |
| 7,699,204 | B2 * | 4/2010 | Viola ......................... 227/175.1 |
| 7,845,536 | B2 * | 12/2010 | Viola et al. ................. 227/179.1 |
| 2001/0007069 | A1 | 7/2001 | Bombard et al. |
| 2002/0010482 | A1 | 1/2002 | Watt |
| 2002/0026159 | A1 | 2/2002 | Zhu et al. |
| 2002/0049454 | A1 | 4/2002 | Whitman et al. |
| 2002/0156150 | A1 | 10/2002 | Williams et al. |
| 2002/0165562 | A1 | 11/2002 | Grant et al. |
| 2002/0173558 | A1 | 11/2002 | Williams et al. |
| 2003/0050590 | A1 | 3/2003 | Kirsch |
| 2003/0073981 | A1 | 4/2003 | Whitman et al. |
| 2003/0073982 | A1 | 4/2003 | Whitman |
| 2003/0089757 | A1 | 5/2003 | Whitman |
| 2003/0111507 | A1 | 6/2003 | Nunez |
| 2003/0236518 | A1 | 12/2003 | Marchitto et al. |
| 2004/0059283 | A1 | 3/2004 | Kirwan et al. |
| 2004/0092960 | A1 * | 5/2004 | Abrams et al. ................. 606/139 |
| 2004/0093029 | A1 | 5/2004 | Zubik et al. |
| 2005/0038471 | A1 | 2/2005 | Chan et al. |
| 2005/0043678 | A1 | 2/2005 | Freyman et al. |
| 2005/0059997 | A1 * | 3/2005 | Bauman et al. ............... 606/219 |
| 2005/0145671 | A1 * | 7/2005 | Viola ......................... 227/175.1 |
| 2005/0184121 | A1 * | 8/2005 | Heinrich .................... 227/175.1 |
| 2006/0085032 | A1 * | 4/2006 | Viola ............................ 606/219 |
| 2006/0085033 | A1 * | 4/2006 | Criscuolo et al. ............. 606/219 |
| 2006/0108393 | A1 * | 5/2006 | Heinrich et al. ........... 227/179.1 |
| 2006/0135992 | A1 * | 6/2006 | Bettuchi et al. ............... 606/219 |
| 2006/0271104 | A1 * | 11/2006 | Viola et al. .................... 606/214 |
| 2009/0078739 | A1 * | 3/2009 | Viola ......................... 227/180.1 |
| 2010/0230466 | A1 * | 9/2010 | Criscuolo et al. ......... 227/179.1 |
| 2011/0036889 | A1 * | 2/2011 | Heinrich et al. ........... 227/175.1 |

FOREIGN PATENT DOCUMENTS

| | | |
|---|---|---|
| JP | 06327683 A | 11/1994 |
| WO | WO 90/05489 A1 | 5/1990 |
| WO | WO 03/105698 A2 | 1/1994 |
| WO | WO 00/56376 A1 | 9/2000 |
| WO | WO 01/62158 A2 | 8/2001 |
| WO | WO 01/62162 A1 | 8/2001 |
| WO | WO 02/30297 A2 | 4/2002 |
| WO | WO 03/088844 A1 | 10/2003 |
| WO | WO 03/088845 A2 | 10/2003 |
| WO | WO 03/094743 A1 | 11/2003 |
| WO | WO 03/094746 A1 | 11/2003 |
| WO | WO 03/105698 A2 | 12/2003 |

OTHER PUBLICATIONS

International Search Report for PCT/US05/37253, completed Apr. 29, 2008. mailed May 28, 2008; 2 pages.

* cited by examiner

STRUCTURE FOR APPLYING SPRAYABLE WOUND TREATMENT MATERIAL

CROSS-REFERENCE TO RELATED APPLICATION

The present application is a Continuation Application claiming the benefit of and priority to U.S. application Ser. No. 11/250,277, filed on Oct. 14, 2005, now U.S. Pat. No. 7,922,743, which in turn claims the benefit of and priority to each of U.S. Provisional Application Ser. No. 60/620,102, filed Oct. 18, 2004, and U.S. Provisional Application Ser. No. 60/620,150, filed on Oct. 18, 2004, the entire contents of each of which being incorporated herein by reference.

BACKGROUND

1. Technical Field

The present disclosure relates to surgical instruments and methods for enhancing properties of tissue repaired or joined by surgical staples and, more particularly to surgical stapling apparatus and structure configured to apply biocompatible wound treatment material.

2. Discussion of Related Art

Throughout the years the medical field has utilized various techniques in an effort to join or bond body tissue together. Historically, suturing was the accepted technique for rejoining severed tissues and closing wounds. Suturing was historically achieved with a surgical needle and a suturing thread, and more recently, with a variety of polymeric or metallic staples, as will be discussed below. The intended function of sutures is to hold the edges of a wound or tissue against one another during the healing process so as to reduce discomfort, pain, scarring and the time required for healing.

Recently, many procedures which in the past required conventional suturing have been replaced by staple suturing which involves the application of the staples to the edges of the wound or tissue with the use of a surgical stapler. Surgical staplers have been developed for joining adjacent tissue, for providing hemostasis of adjacent tissue and for providing hemostasis in conjunction with cutting of adjacent tissue. Such surgical staplers include both linear and annular type configurations. A typical linear stapler and cutter includes parallel rows of staples with a slot for a cutting means to travel between the rows of staples.

Typical linear type staplers are disclosed in commonly assigned U.S. Pat. No. 6,045,560 to McKean et al., U.S. Pat. No. 6,032,849 to Mastri et al., and U.S. Pat. No. 5,964,394 to Robertson, the entire contents of each of which are incorporated herein by reference. A typical annular stapler and cutter, including a plurality of annular rows of staples, typically two, and an annular blade disposed internal of the rows of staples, is disclosed in commonly assigned U.S. Pat. No. 5,799,857 to Robertson et al. and U.S. Pat. No. 5,915,616 to Viola et al., the entire contents of each of which are incorporated herein by reference.

These types of surgical staplers secure adjoining body tissue for improved cutting, join layers of tissue to one another and provide hemostasis by applying parallel or annular rows of staples to surrounding tissue as the cutting means cuts between the parallel or annular rows. Accordingly, by enabling a surgeon to perform all of these tasks simultaneously, surgical staplers have been effective in decreasing the amount of time it takes to fasten tissue together. To even further enhance joining and hemostasis in instances where the stapler is used in highly vascularized tissue, surgical staplers with multiple rows of staples have been used with a high degree of success.

Other surgical procedures utilize pledgets, buttresses or other types of reinforcement materials and fabrics. These buttresses are typically placed over the tissue contacting surface of the anvil and/or the tissue contacting surface of the cartridge of the surgical stapling instrument and secured against the target tissue during the firing of the surgical stapling instrument. Reference may be made to U.S. Pat. No. 5,542,594, the entire content of which is incorporated herein by reference, for a more detailed discussion of the use of buttresses in cooperation with surgical stapling instrument.

Still other surgical procedures involve the step of applying (e.g., by spraying, brushing, etc.) an adhesive material and/or a sealant material to the external surface of the target surgical site following the surgical stapling procedure.

Another procedure which has been developed includes the use of biological tissue adhesives have recently been developed for tissue repair and the creation of anastomoses. Generally, biological adhesives bond separated tissues together to aid in the healing process and to enhance the tissue strength. Such adhesives may be used instead of suturing and stapling for example in surgical procedures for the repair of tissue or the creation of anastomoses.

The application of a suitable biocompatible adhesive offers many advantages to the patient and the surgeon alike such as, for example, the avoidance of penetration of tissue by needles and/or staples, as well as the immediate sealing of the tissue being treated. Moreover, use of a biocompatible adhesive tends to minimize foreign body reaction and scarring. Despite these advantages, however, the weakness along the tissue seam remains as a primary disadvantage in the use of biocompatible adhesives.

Therefore, there is a need for surgical stapler instruments, for example surgical fasteners or staplers which reduce the trauma suffered by a patient, reduce the number of gaps between or at individual staple sites, reduce leakage of fluids, reduce bleeding, and/or which create a relatively strong bond between adjacent body tissues, e.g., along staple lines and tissue seams.

SUMMARY

The present disclosure relates to surgical instruments, structures and methods for enhancing the properties of tissue to be repaired or joined.

According to an aspect of the present disclosure, a surgical stapling apparatus is provided including a body portion; an actuation assembly operatively supported at a proximal end of the body portion; a staple pusher member operatively disposed at a distal end of the body portion and being operatively connected to the actuation assembly for expelling an annular array of staples from the body portion; an anvil assembly movably mounted at the distal end of the body portion for movement toward and away from the staple pusher member; an approximation assembly extending between the body portion and the anvil assembly for moving the anvil toward and away from the tubular body portion; and a wound treatment material dispersion system for delivering wound treatment material to a target surgical site. The dispersion system includes an aperture formed in the anvil assembly oriented to dispense wound treatment material in an outward direction; and a source of wound treatment material in fluid communication with the aperture of the anvil assembly.

In an embodiment, the dispersion system may include a nozzle supported on an anvil member of the anvil assembly, and wherein the aperture formed in the anvil assembly is provided in the nozzle. The dispersion system includes a lumen extending through a stem of the anvil assembly which is in fluid communication with the aperture formed in the nozzle. The lumen of the stem of the anvil assembly may be capable of fluid communication with the source of wound treatment material.

The surgical stapling apparatus may be configured and adapted to dispense wound treatment material onto the target surgical site at least one of before, during and after firing of the surgical stapling apparatus.

According to another embodiment of the disclosure, the source of wound treatment material of the dispersion system is an ampoule which may be selectively positionable within a stem of the anvil assembly. The ampoule may be constructed from a breakable material. Accordingly, during use, upon compression of the ampoule, wound treatment material may be released from the ampoule for transmission to the aperture of the anvil assembly.

The dispersion system includes a piston configured and dimensioned for insertion into the stem of the anvil assembly to rupture the ampoule and force wound treatment material out through the aperture of the anvil assembly and onto the target surgical site at least one of before, during and after firing of the surgical stapling apparatus.

The ampoule defines a lumen therethrough and may include a plunger slidably positioned within the lumen thereof. The lumen of the ampoule may be in fluid communication with the aperture of the anvil assembly when the ampoule is positioned within the stem of the anvil assembly. The dispersion system may include a piston configured and dimensioned for insertion into the lumen of the ampoule to engage the plunger and to force the plunger through the lumen of the ampoule to dispense wound treatment material out through the aperture of the anvil assembly and onto the target surgical site at least one of before, during and after firing of the surgical stapling apparatus.

In an embodiment, the dispersion system may include at least one drape supported on and substantially surrounding a stem of the anvil assembly. The drape includes an undeployed condition in which the drape is in relatively close proximity to the stem of the anvil assembly, and a deployed condition in which the drape is in relatively spaced relation to the stem of the anvil assembly. Desirably, the dispersion system includes a first drape positioned distally of the aperture of the anvil assembly and a second drape positioned proximally of the aperture of the anvil assembly. Accordingly, in use, when the drapes are in the deployable condition, the drapes direct the dispersion of the wound treatment material.

It is envisioned that a stem of the anvil assembly may include an annular groove formed proximally and distally of the aperture of the anvil assembly. The surgical stapling apparatus may further include an annular blade retractably disposed at a distal end of the body portion, wherein the annular blade includes a plurality of openings formed therein.

In an embodiment, the dispersion system may include a plurality of tubular members supported within a lumen of a stem of the anvil assembly. The tubular members define the source of wound treatment material. The tubular members have an undeployed condition in which the tubular members are disposed within the lumen of the stem, and a deployed condition in which the tubular members project from windows formed in the stem of the anvil assembly. Accordingly, in use, when the tubular members are actuated from the undeployed to the deployed condition, the tubular members rupture to dispense wound treatment material.

According to another aspect of the present disclosure, a surgical stapling apparatus is provided and includes a body portion; an actuation assembly operatively supported at a proximal end of the body portion; a staple pusher member operatively disposed at a distal end of the body portion and being operatively connected to the actuation assembly for expelling an annular array of staples from the body portion; an anvil assembly movably mounted at the distal end of the body portion for movement toward and away from the staple pusher member; an approximation assembly extending between the body portion and the anvil assembly for moving the anvil toward and away from the tubular body portion; and a wound treatment material dispersion system for delivering wound treatment material to a target surgical site. The dispersion system includes a plurality of needles retractably supported in needle receiving slots provided in the staple pusher member, wherein when the surgical stapling apparatus is fired the needles penetrate the target tissue and dispense wound treatment material; and a source of wound treatment material associated with each needle receiving slot.

In an embodiment, the source of wound treatment material may include a capsule disposed within each needle receiving slot. The dispersion system may include a finger disposed in each needle receiving slot, wherein upon firing of the surgical stapling apparatus the fingers are advanced through the needle receiving slots to rupture the capsules, to deploy the needles, and to push the wound treatment material through the needles.

According to a further aspect of the present disclosure, a splash guard for use in combination with an anastomotic surgical stapling apparatus is provided. The surgical stapling apparatus is desirably configured and adapted to deliver wound treatment material to a target surgical site. Accordingly, the splash guard includes a central hub defining a lumen therethrough for receiving a stem of an anvil assembly of the surgical stapling apparatus; and an annular cuff supported on the central hub and extending at least substantially therearound, wherein the annular cuff is disposed radially outward of a staple line of the surgical stapling apparatus.

The splash guard may further include at least one spoke interconnecting the annular cuff to the central hub. It is envisioned that at least the annular cuff and the at least one spoke are fabricated from a bio-absorbable material. The annular cuff may be concave and may define an upper rim and a lower rim, wherein the upper and lower rims are dimensioned to contact an outer surface of the target surgical site.

According to yet another embodiment of the present disclosure, a wound treatment material dispersion system for use in combination with an anastomotic surgical stapling apparatus is provided. The surgical stapling apparatus may include an anvil assembly supported opposite a staple pusher member. The wound treatment material dispersion system includes a disc defining an outer edge and an inner edge, the disc including a plurality of apertures formed therethrough; at least one of an annular inner wall integrally connected to the inner edge of the disc and an annular outer wall integrally connected to the outer edge; and wound treatment material disposed on a surface of the disc.

The inner annular wall of the wound treatment material dispersion system is configured and dimensioned for positioning inwardly of the staple pusher member, and wherein the outer annular wall of the wound treatment material dispersion system is configured and dimensioned for positioning outwardly of the staple pusher member. Desirably, the inner annular wall and the outer annular wall are disposed along one side of the disc.

According to a further aspect of the present disclosure, a method of performing a surgical anastomosis procedure is provided. The method includes the step of providing a surgical stapling apparatus having an anvil assembly movably mounted with respect to a body portion and a wound treatment material dispersion system for dispensing wound treatment material onto a target surgical site. The wound treatment material dispersion system includes an aperture formed in the anvil assembly oriented to dispense wound treatment material in an outward direction; and a source of wound treatment material in fluid communication with the aperture of the anvil assembly. The method further includes the steps of disposing an anvil assembly into a first intestinal section and surgically securing the first intestinal section to the anvil assembly; disposing a distal end portion of the surgical stapling apparatus into a second intestinal section and surgically securing the second intestinal section to the distal end of the surgical stapling apparatus; connecting the anvil assembly to the distal end portion of the surgical stapling apparatus; actuating the wound treatment material dispersion system to dispense wound treatment material along an inner surface and between the first and the second intestinal sections; and approximating the anvil assembly toward the tubular body portion.

The wound treatment material may be dispensed from at least one of an anvil member and an anvil stem of the anvil assembly. The wound treatment material may be contained within an ampoule in the stem of the anvil assembly. Accordingly, the method may further include the step of firing the surgical stapling apparatus in order to release the wound treatment material from the ampoule and to dispense the wound treatment material from the aperture of the anvil assembly.

The dispersion system may include a piston configured and adapted for engagement with the ampoule disposed within the stem of the anvil assembly. Accordingly, the method may further include the step of advancing the piston to release the wound treatment material from the ampoule and to dispense the wound treatment material from the aperture of the anvil assembly.

In an embodiment, the dispersion system may include at least one drape supported on and substantially surrounding a stem of the anvil assembly. The drape includes an undeployed condition in which the drape is in relatively close proximity to the stem of the anvil assembly, and a deployed condition in which the drape is in relatively spaced relation to the stem of the anvil assembly. Accordingly, the method may include the step of deploying the drape prior to dispersing wound treatment material. As such, when the drapes are in the deployable condition, the drapes direct the dispersion of the wound treatment material.

The method may further include the step of placing a splash guard over the stem of the anvil assembly prior to the connecting of the anvil assembly to the distal end portion of the surgical stapling apparatus.

The splash guard may include a central hub defining a lumen therethrough for receiving a stem of an anvil assembly of the surgical stapling apparatus; and an annular cuff supported on the central hub and extending at least substantially therearound, wherein the annular cuff is disposed radially outward of a staple line of the surgical stapling apparatus. The splash guard may further include at least one spoke interconnecting the annular cuff to the central hub. It is envisioned that at least the annular cuff and the at least one spoke are fabricated from a bio-absorbable material. The annular cuff may be concave and may define an upper rim and a lower rim, and wherein when the splash guard is disposed on the stem of the anvil assembly and the anvil assembly is approximated toward the distal end portion of the surgical stapling apparatus, the upper and lower rims of the annular cuff are dimensioned to contact an outer surface of the first and second intestinal sections.

According to still another aspect of the present disclosure, a method of performing a surgical anastomosis procedure is provided. The method includes the steps of providing a surgical stapling apparatus having an anvil assembly movably mounted with respect to a body portion and a wound treatment material dispersion system for dispensing wound treatment material onto a target surgical site. The wound treatment material dispersion system includes a plurality of needles retractably supported in needle receiving slots provided in the staple pusher member, wherein when the surgical stapling apparatus is fired the needles penetrate the target tissue and dispense wound treatment material; and a source of wound treatment material associated with each needle receiving slot. The method further includes the steps of disposing an anvil assembly into a first intestinal section and surgically securing the first intestinal section to the anvil assembly; disposing a distal end portion of the surgical stapling apparatus into a second intestinal section and surgically securing the second intestinal section to the distal end of the surgical stapling apparatus; connecting the anvil assembly to the distal end portion of the surgical stapling apparatus; approximating the anvil assembly toward the tubular body portion; and actuating the wound treatment material dispersion system to inject the plurality of needles into at least one of the first and second intestinal sections and to dispense wound treatment material through the needles.

The source of wound treatment material may include a capsule disposed within each needle receiving slot at a location proximal of the needle. The dispersion system may include a finger disposed in each needle receiving slot. Accordingly, the method may include the step of firing the surgical stapling apparatus to advance the fingers through the needle receiving slots to rupture the capsules, to deploy the needles, and to push the wound treatment material through the needles.

In any of the embodiments disclosed above, the wound treatment material is at least one of an adhesive, a sealant, a hemostat, and a medicament.

BRIEF DESCRIPTION OF THE DRAWINGS

The foregoing features of the present disclosure will become more readily apparent and may be understood by referring to the following detailed description of an illustrated embodiment of a surgical instrument, apparatus or structure, taken in conjunction with the accompanying drawings, in which.

DETAILED DESCRIPTION OF THE EMBODIMENT

Figure 1:
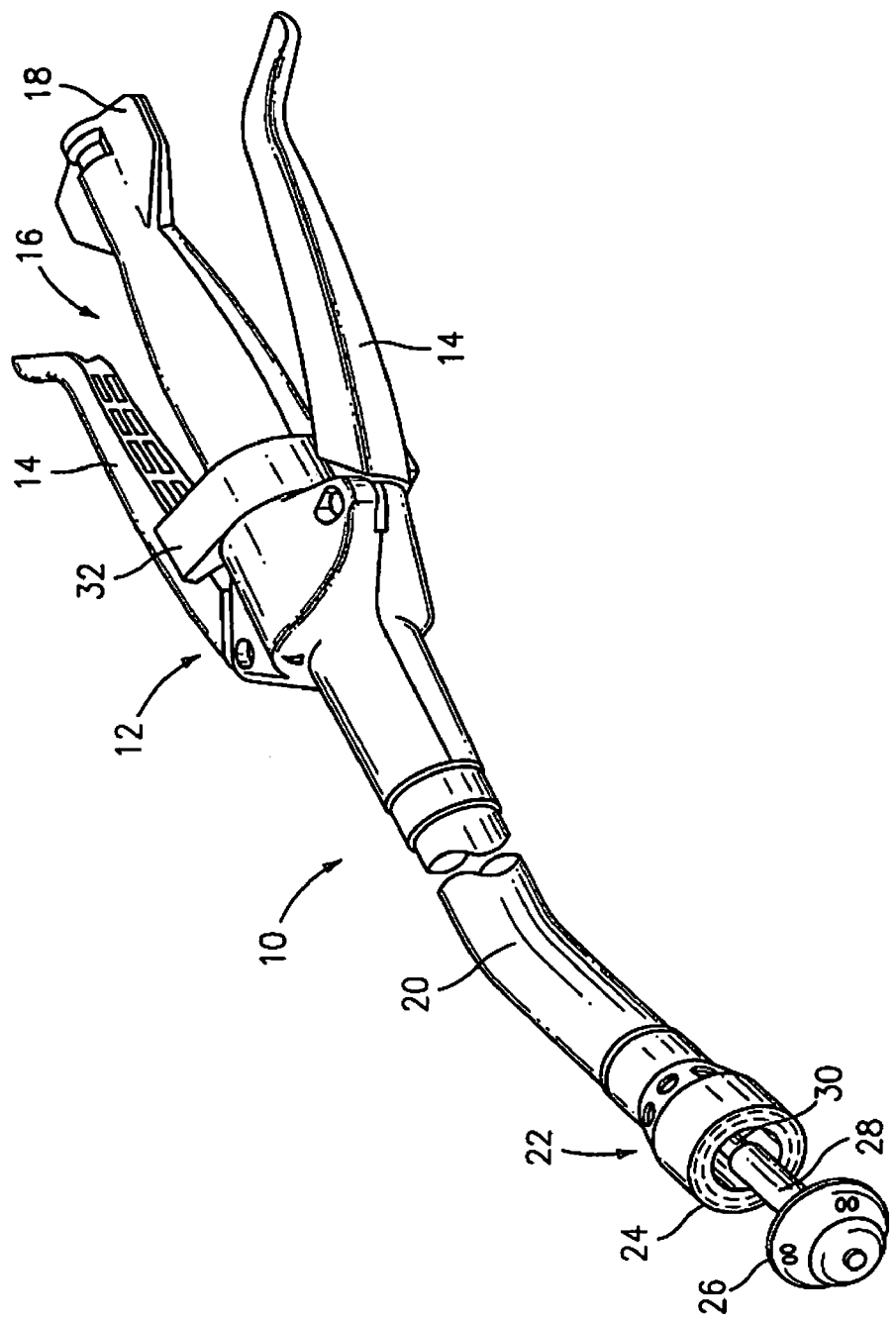
FIG. 1 illustrates a perspective view of a surgical stapling apparatus according to an embodiment of the present disclosure.

Embodiments of the presently disclosed surgical stapling apparatus will now be described in detail with reference to the drawing figures wherein like reference numerals identify similar or identical elements. As used herein and as is traditional, the term "distal" refers to that portion which is furthest from the user while the term "proximal" refers to that portion which is closer to the user.

Referring now in specific detail to the drawings, in which like reference numerals identify similar or identical elements throughout the several views, FIG. 1 shows a surgical stapling apparatus 10 which employs the structure for applying a dispersible wound treatment material in accordance with the present disclosure. Apparatus 10 includes a handle assembly 12 having at least one pivotable actuating handle member 14, and further includes advancing means 16. Advancing means 16 includes a rotatable grip member 18 whose function will be described below.

Extending from handle assembly 12, there is provided a tubular body portion 20 which may be constructed so as to have a curved shape along at least a portion of its length. Tubular body portion 20 may also be straight, or in other embodiments, tubular body portion 20 may be flexible to bend to any configuration. Body portion 20 terminates in a staple pusher member 22. Staple pusher member 22 includes an annular array of staples 24. Positioned opposite staple pusher member 22 is provided an anvil member 26 which is connected to apparatus 10 by stem 28 at connection means 30. Anvil member 26 and staple pusher member 22 are disclosed in commonly assigned U.S. Pat. No. 5,119,983, issued Jun. 9, 1992, which is incorporated herein by reference.

While apparatus 10 is shown and described as utilizing a staple pusher member having an annular array of staples positioned on the tubular body portion, and having the anvil member positioned opposite the staple pusher member for movement towards and away from the staple pusher member, it is of course contemplated that the anvil member may be positioned on the tubular body portion and the staple pusher member and array of staples be positioned opposite the anvil member for movement towards and away from the anvil member. Such a construction is to be considered within the scope of the present disclosure.

In operation, apparatus 10 is positioned within a tubular organ in the body of the patient and the ends of the organ to be joined are positioned in the gap between staple pusher member 22 and anvil member 26 so that anvil member 26 is fully extended. As is conventional, the ends of the organ may be secured over anvil member 26 and staple pusher member 22 by a purse string suture prior to approximation of anvil member 26 in relation to staple pusher member 22. With anvil member 26 and staple pusher member 22 purse string sutured, stem 28 of anvil member 26 is coupled to connection means 30 disposed within staple pusher member 22.

In order to approximate anvil member 26 towards staple pusher member 22, grip member 18 is rotated to displace an inner rod member (not shown) in a proximal direction. This draws anvil member 26 into position adjacent staple pusher member 22 and locates the ends of the tissue between these two members.

Once the proper distance is set between anvil member 26 and staple pusher member 22 interlock means 32 may be released and actuating handles 14 may be pivoted to drive the staples through the tissue and against anvil member 26 to complete the circular anastomosis of the tubular organ. Reference may be made to U.S. Pat. No. 5,119,983, previously incorporated herein by reference for a more detailed description and discussion of the structure and operation of surgical stapling apparatus 10.

Figure 2:
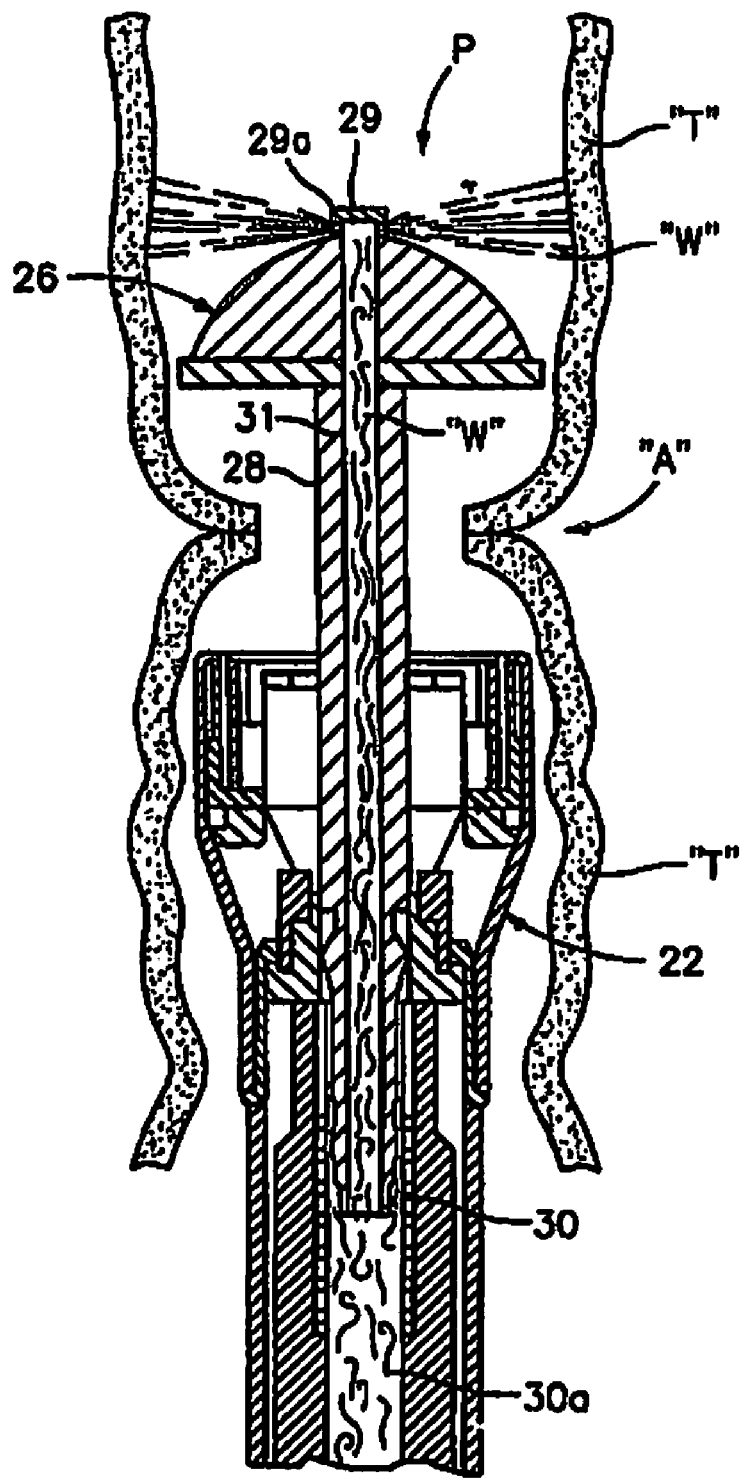
FIG. 2 is a longitudinal cross-sectional view of the distal end of a surgical stapling apparatus including a wound treatment material dispersion system in accordance with an embodiment of the present disclosure, wherein the surgical stapling apparatus is positioned within the operative site such that the anvil member is positioned distally of the anastomosis site and the surgical stapling apparatus is dispensing wound treatment material.
Figure 3:
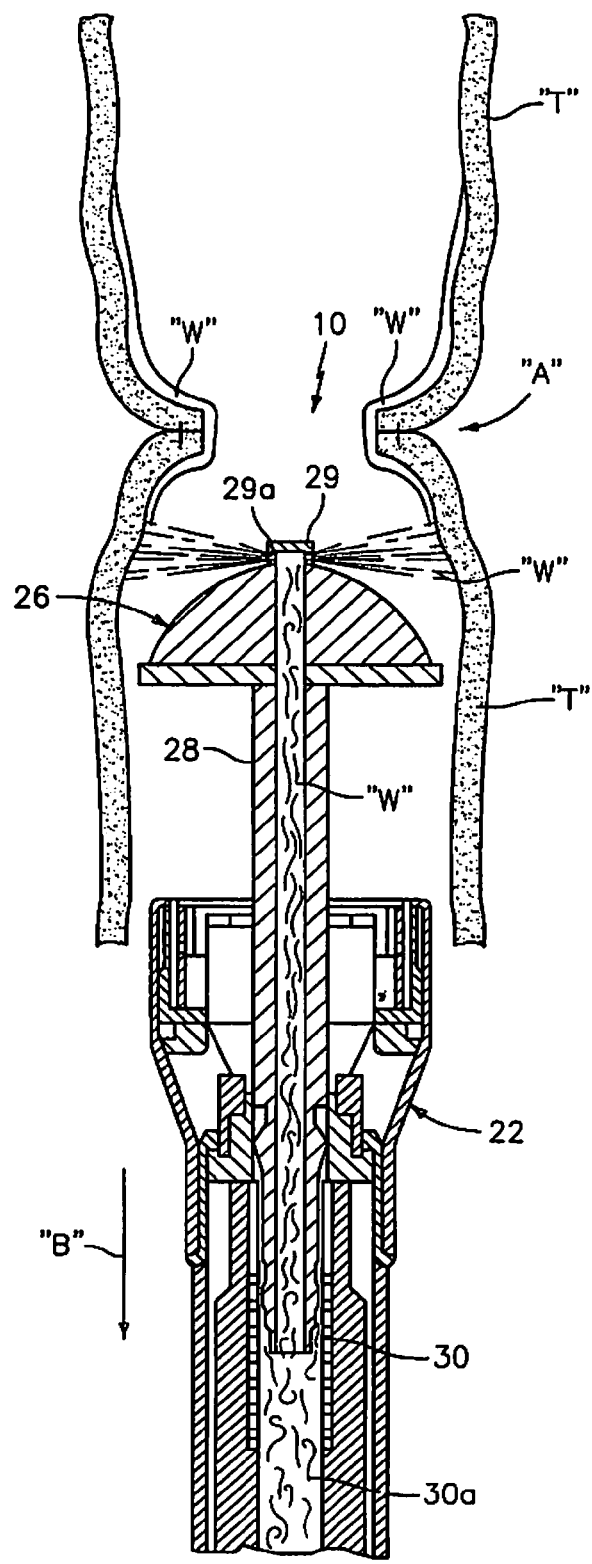
FIG. 3 is a longitudinal cross-sectional view of the surgical stapling apparatus of FIG. 2, wherein the anvil member is positioned proximally of the anastomosis site and the surgical stapling apparatus is dispensing wound treatment material.

Turning now to FIGS. 2 and 3, surgical stapling apparatus 10 may include, according to an embodiment of the present disclosure, a wound treatment material dispersion system configured to disperse (e.g., spray, eject, squeeze, dispense, etc.) wound treatment material "W" onto the inner surface of the anastomosed tissue "T". The dispersion system includes a dispersion head or nozzle 29 provided at the distal end of anvil member 26, and a lumen 31 extending through stem 28 of anvil member 26 and terminating in at least one radially oriented channel 29a formed in dispersion head 29. Lumen 31 is fluidly connected to a source of fluid, i.e., wound treatment material "W", saline, etc. (not shown). When anvil member 26 is connected to the distal end of surgical stapling apparatus 10, lumen 31 of stem 28 is fluidly connected to/with a lumen 30a provided in connection means 30. It is envisioned that lumen 30a of connection means 30 interconnects lumen 31 of anvil member 26 to the source of fluid.

In use, as seen in FIGS. 2 and 3, following firing of surgical stapling apparatus 10, anvil member 26 is spaced from staple pusher member 22 in order to release the tissue "T" clamped therebetween. With anvil member 26, and particularly dispersion head 29, disposed distally of the anastomosis site "A", wound treatment material "W" is forced through lumen 30a of connection means 30, through lumen 31 of anvil member 26 and radially outward from channels 29a of dispersion head 29.

As wound treatment material "W" is being dispersed from channels 29a of dispersion head 29, surgical stapling apparatus 10 is withdrawn in a proximal direction, as indicated by arrow "B" (see FIG. 3), until dispersion head 29 is disposed at a location proximal of the anastomosis site "A". In so doing, wound treatment material "W" is applied to the inner surface of the tissue "T" from a location distal of the anastomosis site "A" to a location proximal of the anastomosis site "A" thereby coating the inner surface of the body lumen in and around the anastomosis site "A".

It is envisioned that application of wound treatment material "W" to the anastomosis site "A" may help to reduce the incidence of anastomotic leakage by sealing the inner lumen of the anastomosis. It is further envisioned that application of wound treatment material "W" to the anastomosis site "A" may help to adhere the anastomosed ends of the tissue "T" to one another.

It is contemplated that the rate of dispersion of wound treatment material "W" from dispersion head 29 is selected such that sufficient wound treatment material "W" is applied to the inner surface of the body lumen in order to effectuate sufficient tissue sealing and adhesion and to not interfere with the flow of materials through the body lumen.

It is envisioned that wound treatment material "W" may be a substantially non-viscous fluid or liquid such that the wound treatment material "W" may freely flow from dispersion head 29. It is further envisioned that the wound treatment material "W" dispended from surgical stapling apparatus 10 may be in the form of a foam which expands to momentarily radially fill the cavity of the body lumen in and around the anastomosis site "A", to thereby completely coat the inner surface thereof with wound treatment material "W", and which collapses after a period of time to re-open the passageway of the body lumen.

Turning now to FIGS. 4-8, a wound treatment material dispersion system, according to an alternate embodiment of the present disclosure, is shown and described. The dispersion system of FIGS. 4-8 includes an anvil member 126 which is connectable to connection means 30 of surgical stapling apparatus 10.

Figure 4:
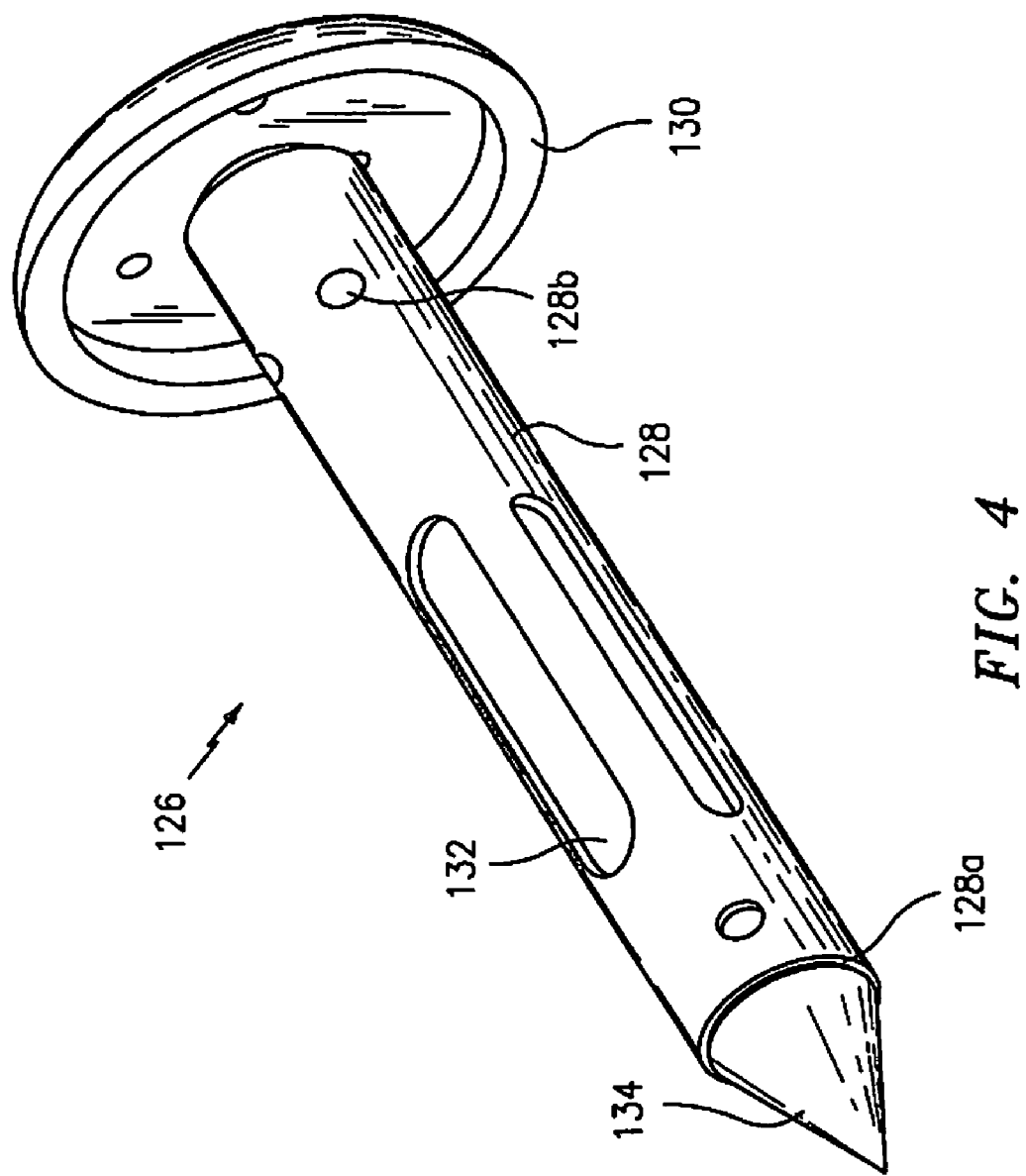
FIG. 4 is a perspective view of an anvil member according to another embodiment of the present disclosure.
Figure 5:
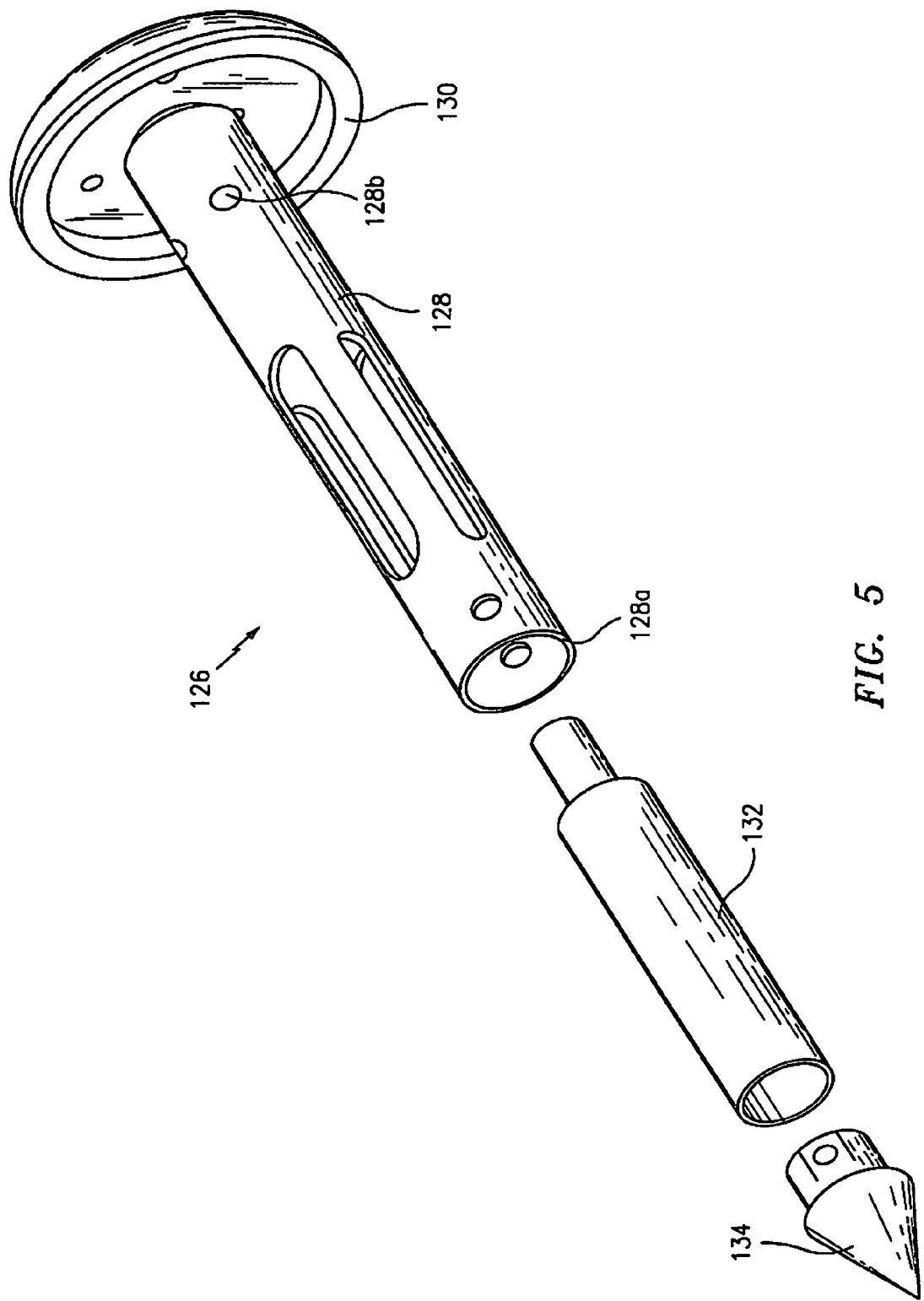
FIG. 5 is perspective view of the anvil member of FIG. 4, with parts separated.
Figure 6:
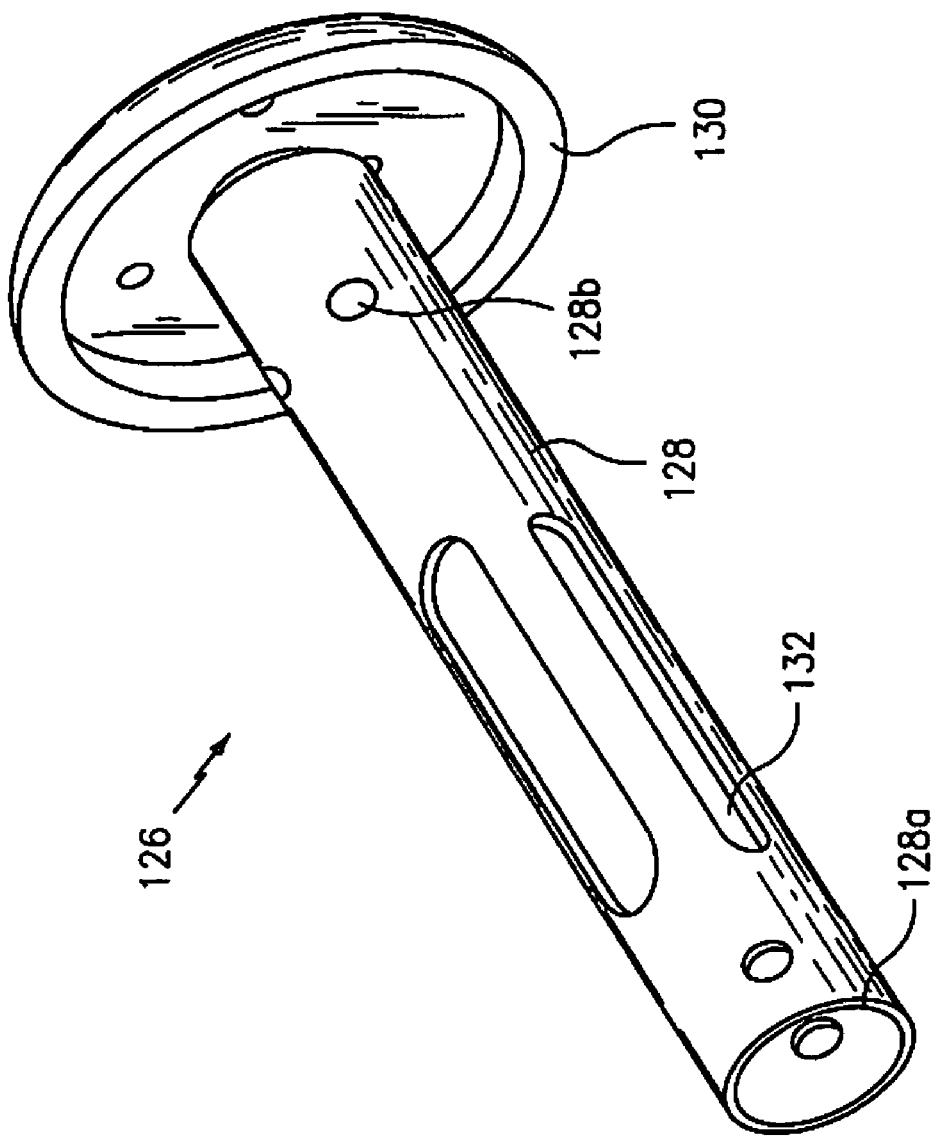
FIG. 6 is a perspective view of the anvil member of FIG. 4 with the tip removed therefrom.

As seen in FIGS. 4-6, anvil member 126 includes a hollow tubular stem 128 having an open proximal end 128a and at least one port 128b formed in a side surface thereof, an anvil head 130 operatively connected to a distal end of stem 128, an ampoule 132 selectively positionable within stem 128, and a tip or cap 134 selectively operatively connectable to proximal end 128a of stem 128 for maintaining ampoule 132 within stem 128.

Ampoule 132 is made from a frangible or breakable material, such as, for example, glass, metal, polymers and the like, and is configured to retain a quantity of a wound treatment material "W" therein. As will be described in greater detail below, the wound treatment material "W", retained in ampoule 132, is dispensed therefrom upon rupturing or breaking of ampoule 132. In particular, as will be discussed in greater detail below, with ampoule 132 positioned within stem 128, ampoule 132 may be ruptured by longitudinally compressing ampoule 132. In so doing, the wound treatment material "W", retained in ampoule 132, is dispersed into stem 128 wherein the force of compression further urges the wound treatment material "W" out through the at least one port 128b.

Figure 7:
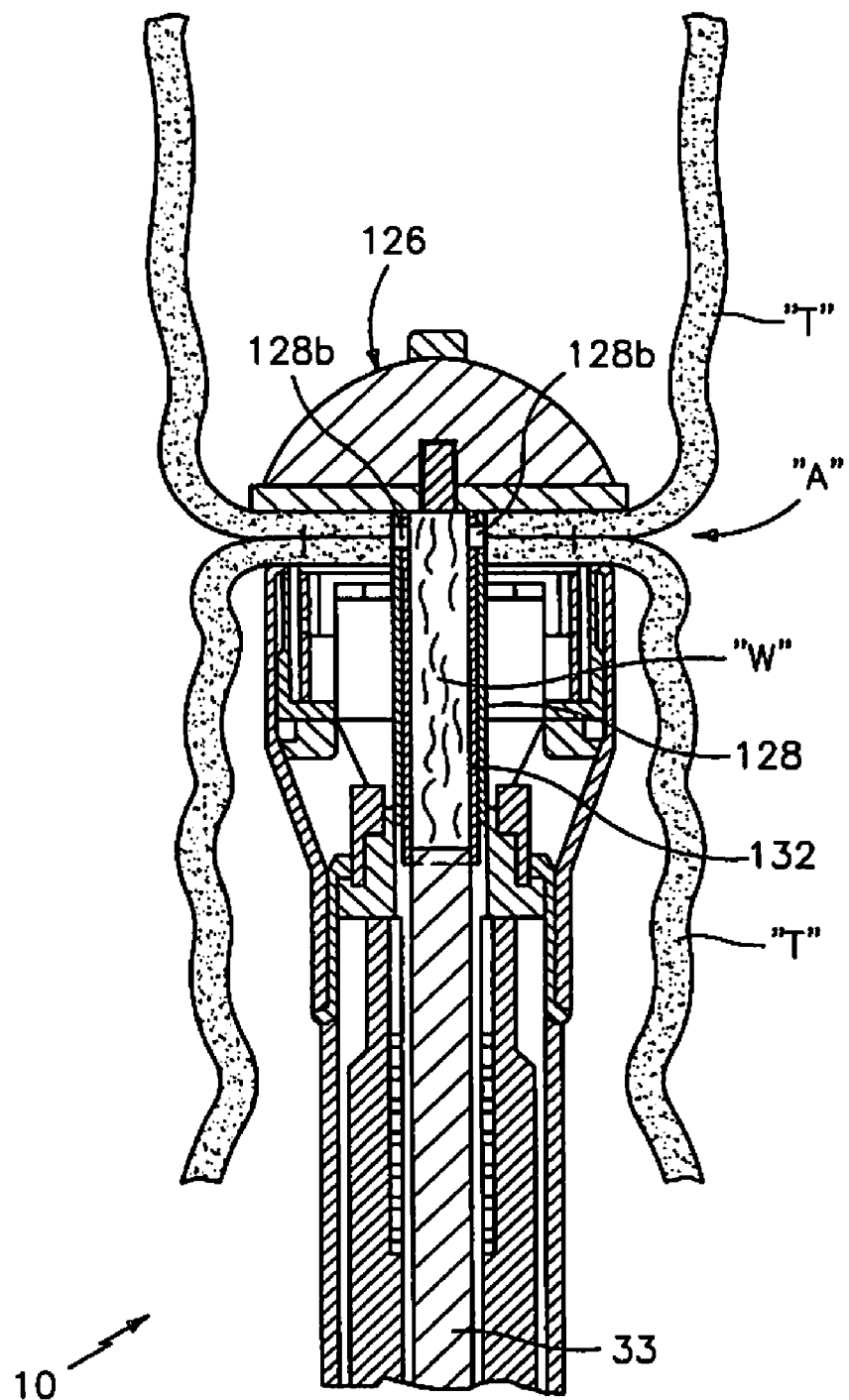
FIG. 7 is a longitudinal cross-sectional view of the surgical stapling apparatus of FIG. 2, with the anvil member of FIGS. 4-6 operatively connected thereto, illustrating the surgical stapling apparatus having the tissue to be anastomosed clamped between the anvil member and the staple pusher member prior to the firing thereof.
Figure 8:
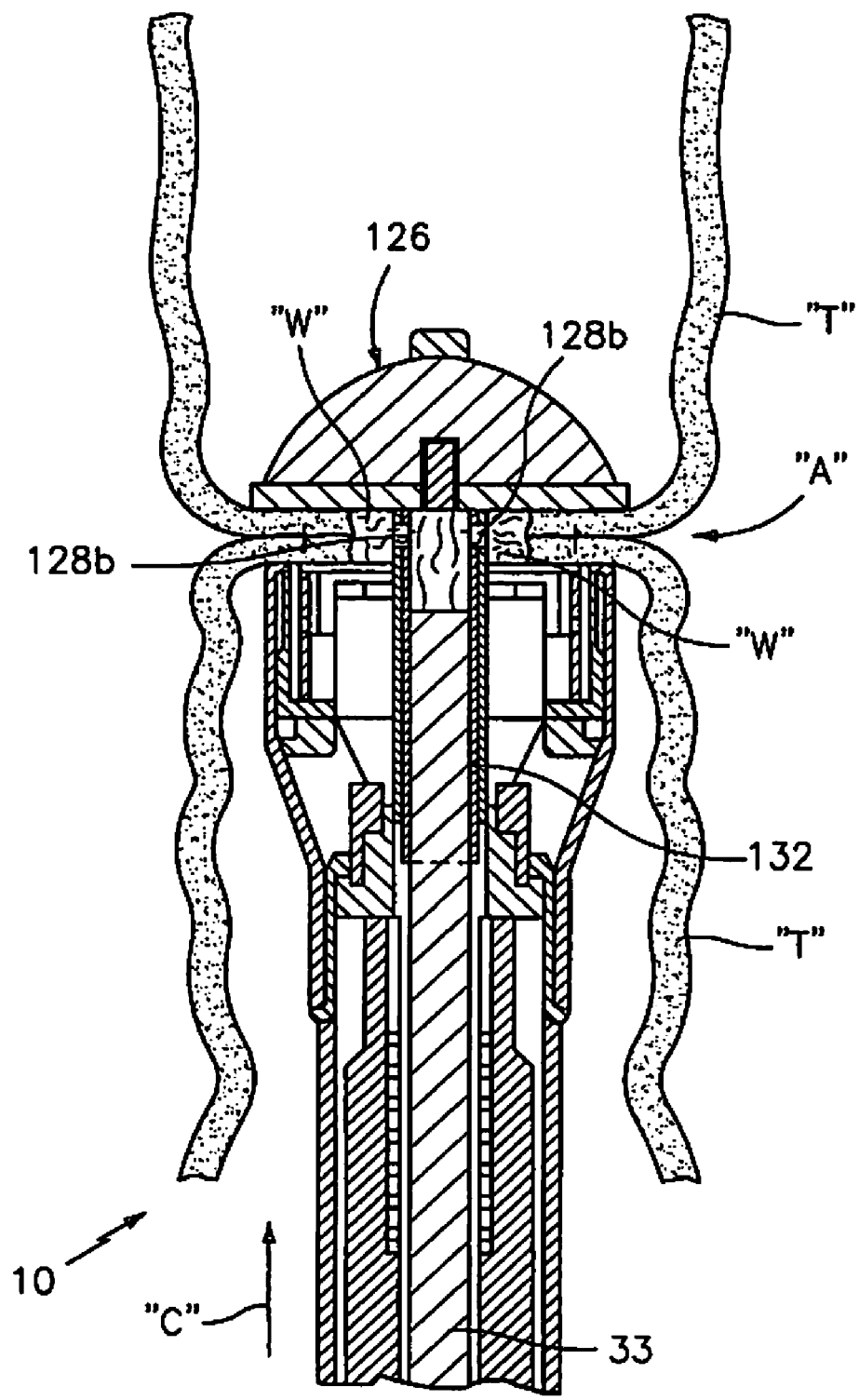
FIG. 8 is a longitudinal cross-sectional view of the surgical stapling apparatus of FIG. 2, with the anvil member of FIGS. 4-6 operatively connected thereto, illustrating the surgical stapling apparatus having the tissue to be anastomosed clamped between the anvil member and the staple pusher member during or after firing of the surgical stapling apparatus.

Turning now to FIGS. 7 and 8, use of the wound treatment material dispersion system of FIGS. 4-6, in connection with surgical stapling apparatus 10, is shown and described. In particular, with ampoule 132 disposed within stem 128 and cap 134 (see FIGS. 4 and 5) secured to proximal end 128a of stem 128, anvil member 126 is introduced into one side of the anastomosis. The tissue "T" is purse string sutured to stem 128 such that the purse string suture is located distally of the at least one port 128b.

As seen in FIG. 7, with anvil member 126 introduced into one side of the anastomosis, cap 134 is removed and stem 128 of anvil member 126 is operatively connected to connection means 30. Connection means 30 includes a piston or plunger 33 having a distal end configured to slidably enter proximal end 128a of stem 128 and engage ampoule 132. With anvil member 126 connected to the distal end of surgical stapling apparatus 10, the surgical procedure is continued as described above.

In the present procedure, when actuating handles 14 are squeezed to fire surgical stapling apparatus 10, as seen in FIG. 8, piston 33 is advanced in the direction of arrow "C", thereby compressing ampoule 132 within stem 128 and causing ampoule 132 to rupture and release the wound treatment material "W" retained therein. With ampoule 132 ruptured, continued squeezing of handles 14 continues to advance piston 33 through stem 128 and squeeze the wound treatment material "W" out of stem 128 through ports 128b. The wound treatment material is thus dispersed onto the anastomosis site "A".

Desirably, the stroke and/or distal advancement of piston 33 is mechanically timed such that piston 33 ruptures ampoule 132 and causes the wound treatment material "W" to disperse either prior to or simultaneously with the firing of the surgical staples.

Figure 9:
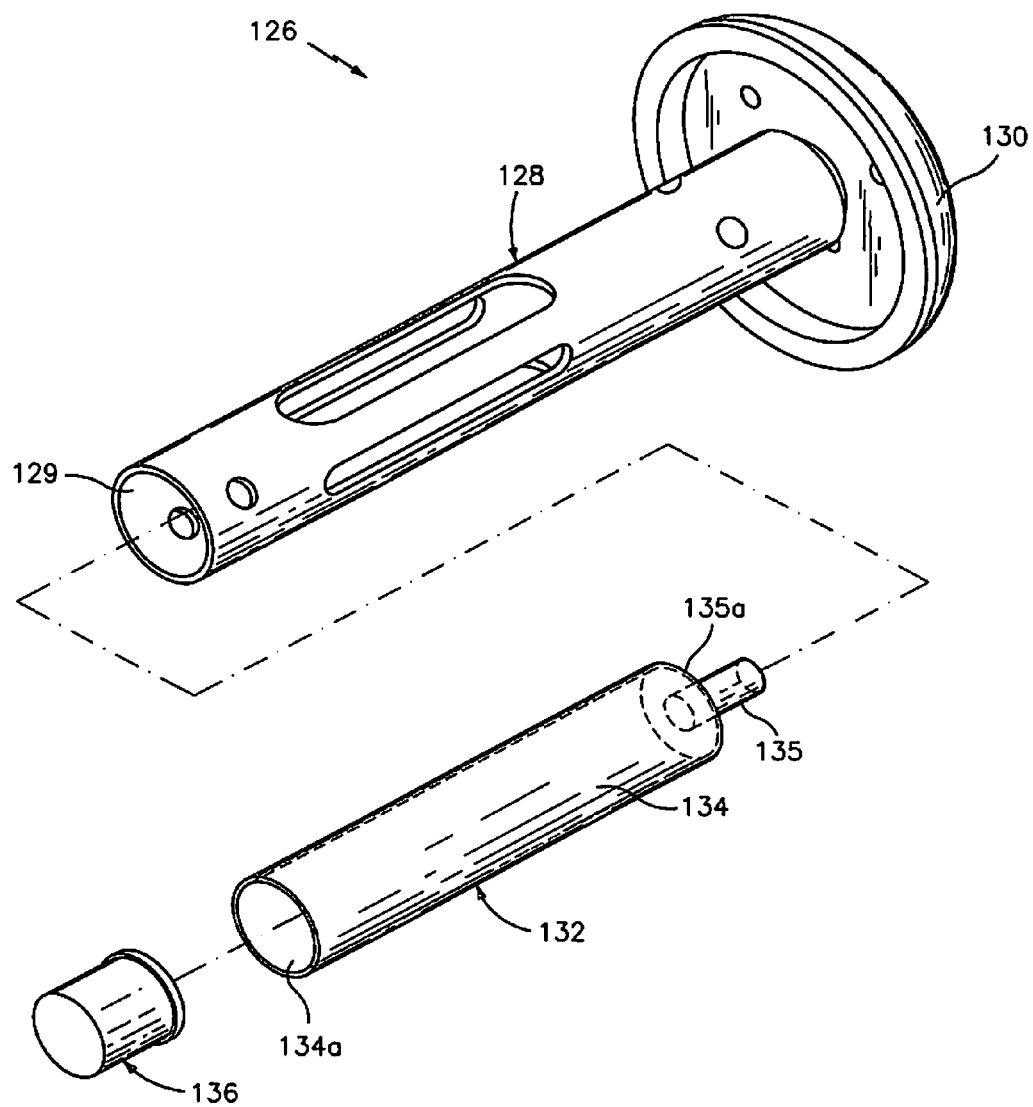
FIG. 9 is a perspective view, with parts separated, of an anvil member according to an alternate embodiment of the present disclosure.
Figure 11:
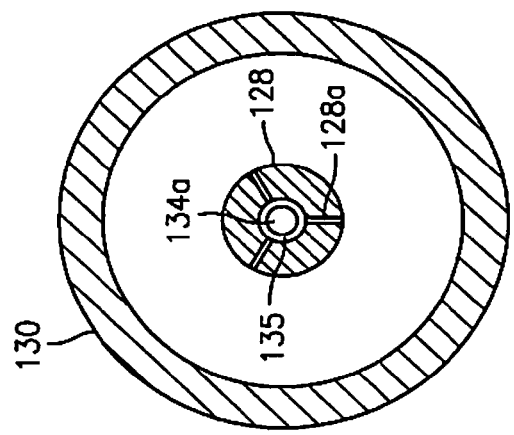
FIG. 11 is a cross-sectional view of the anvil member of FIGS. 9 and 10, as taken through 11-11 of FIG. 10.
Figure 10:
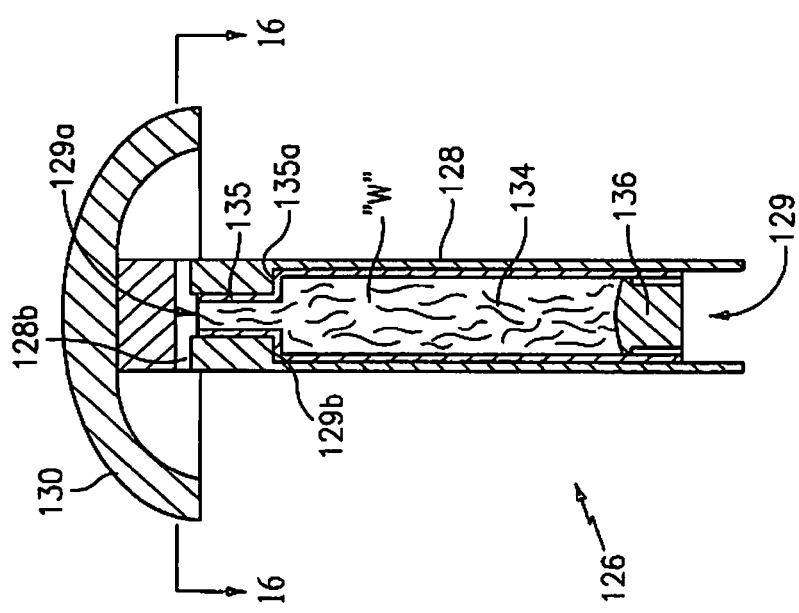
FIG. 10 is a schematic longitudinal cross-sectional view of the anvil member of FIG. 9.

Turning now to FIGS. 9-11, a wound treatment material dispersion system, according to yet another embodiment of the present disclosure, is shown and described. The dispersion system of FIGS. 9-11 is substantially similar to the dispersion system of FIGS. 4-8 and thus will only be discussed in detail to the extent necessary to identify differences in construction and operation.

As seen in FIGS. 9-12, ampoule 132 includes a body portion 134 having a nub 135 extending axially therefrom, and defining a lumen 134a through each of body portion 134 and nub 135. Nub 135 has a smaller cross-sectional dimension than body portion 134 and defines a shoulder 135a. Ampoule 132 further includes a plunger 136 slidably disposed within lumen 134a. Plunger 136 forms a fluid tight seal with the inner surface of body portion 134. Desirably, wound treatment material "W" is retained within lumen 134a of ampoule 132.

Figure 12:
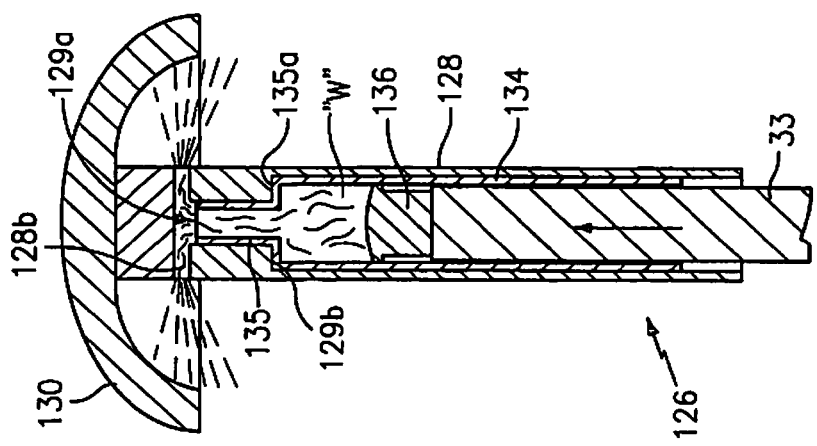
FIG. 12 is a schematic longitudinal cross-sectional view of the anvil member of FIGS. 9-11, illustrating the dispersion of wound treatment material therefrom.

Stem 128 of anvil member 126 defines a cavity 129 for selectively receiving ampoule 132 therein. As seen in FIGS. 11-12, a distal end of cavity 129 defines a distal pocket 129a configured to receive nub 135 of ampoule 132 therein. Pocket 129a is dimensioned such that shoulder 135a of ampoule 132 contacts or engages a corresponding shoulder 129b formed in cavity 129.

Desirably, as seen in FIGS. 11-12, ports 128b of stem 128 are in fluid communication with pocket 129a of cavity 129. Preferably, ports 128b are formed at a location distal of a distal-most surface of nub 135. In this manner, when ampoule 132 is placed within cavity 129 of stem 128, lumen 134a of ampoule 132 is in fluid communication with ports 128b. As seen in FIG. 11, ports 128b define a manifold to divide the dispersion of wound treatment material to different radial segments around stem 128.

As seen in FIG. 12, in operation, upon distal advancement of plunger 136 through lumen 134a of ampoule 132, wound treatment material "W" is forced through nub 135, into distal pocket 129a, and out through ports 128b. It is envisioned that a piston 33, or some other device or method (e.g., pneumatic) may be used to advance plunger 136 distally through lumen 134a.

Figure 13:
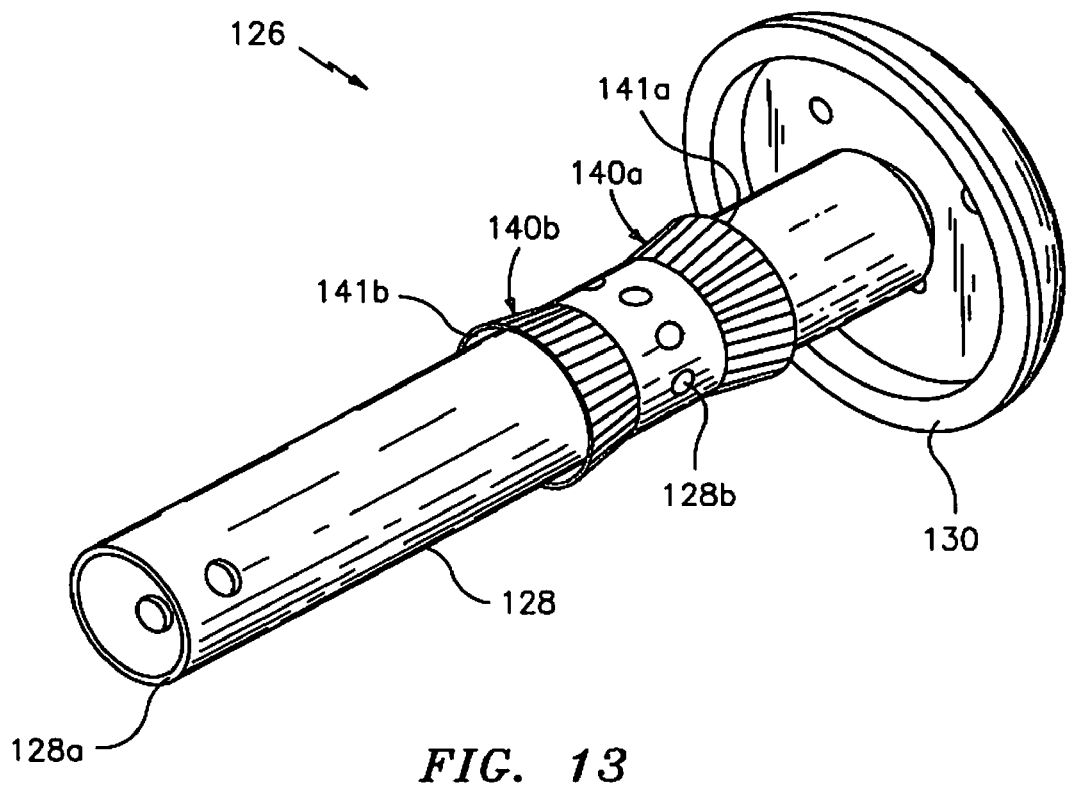
FIG. 13 is a perspective view of an alternate embodiment of the anvil member of FIGS. 4-6, shown in an un-deployed condition.
Figure 14:
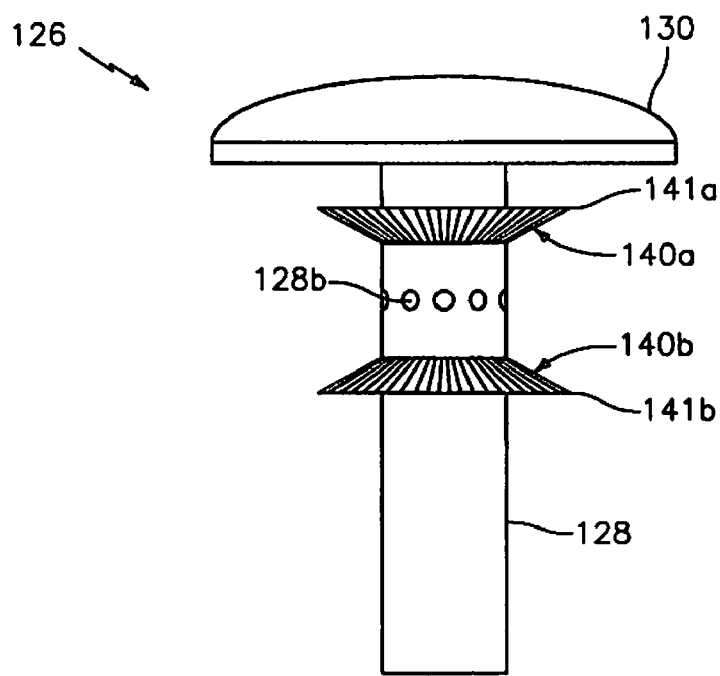
FIG. 14 is a side elevational view of the anvil member of FIG. 12, shown in a deployed condition.
Figure 15:
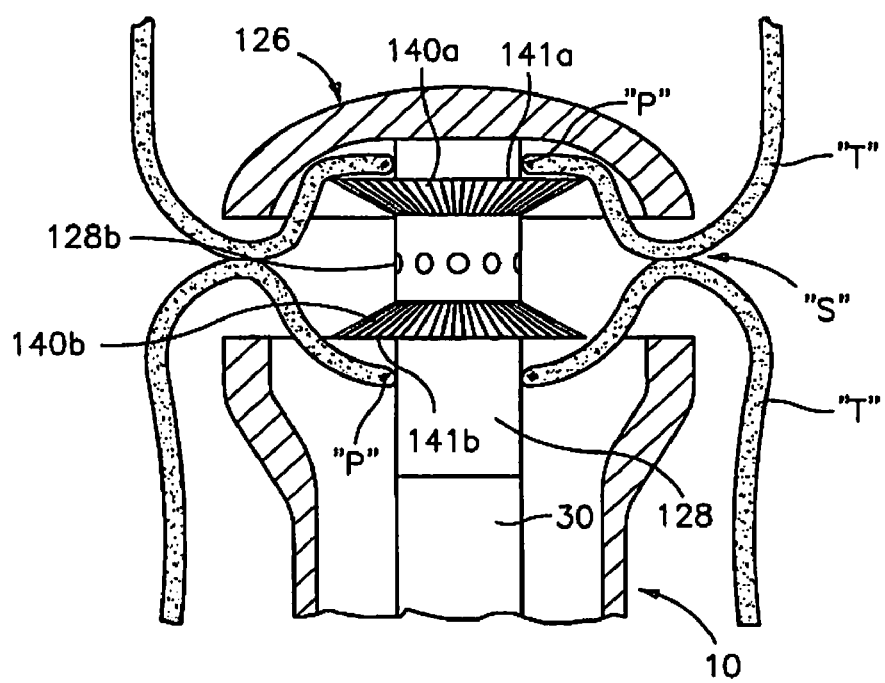
FIG. 15 is a schematic longitudinal cross-sectional view of the anvil member of FIGS. 12 and 13 operatively connected to the distal end of the surgical stapling apparatus and illustrating the target tissue clamped between the anvil member and the staple pusher member.

Turning now to FIGS. 13-15, a wound treatment material dispersion system, according to yet another embodiment of the present disclosure, is shown and described. The dispersion system of FIGS. 13-15 is substantially similar to the dispersion system of FIGS. 4-8 and thus will only be discussed in detail to the extent necessary to identify differences in construction and operation.

As seen in FIGS. 13-15, anvil member 126 includes a first expandable drape 140a operatively connected to and at least substantially surrounding stem 128 at a location distal of ports 128b, and a second expandable drape 140b operatively connected to and at least substantially surrounding stem 128b at a location proximal of ports 128b. Drapes 140a, 140b have an un-deployed orientation, as seen in FIG. 13, in which the respective outer radial edge 141a, 141b of drapes 140a, 140b are in close proximity to and/or in contact with the outer surface of stem 128, and a deployed orientation, as seen in FIG. 14, in which outer radial edges 141a, 141b of drapes 140a, 140b are spaced a radial distance from the outer surface of stem 128.

It is envisioned and within the scope of the present disclosure, that drapes 140a, 140b may be maintained in the un-deployed orientation by a tear-away or break-away sleeve or liner (not shown) which surrounds drapes 140a, 140b. Accordingly, drapes 140a, 140b may be deployed by tearing away the sleeve or liner. It is further contemplated that each drape 140a, 140b may be fabricated from a flexible material, wherein the inner radial edge thereof is secured to the outer surface of stem 128 and the outer radial edge thereof may include a shape memory alloy hoop or ring operatively connected therewith. In this manner, the ring may have a collapsed or biased condition in which the ring is in close proximity to the outer surface of stem 128, to maintain the flexible material in an un-expanded condition, and an expanded or un-biased condition in which the ring extends a radially distance from the outer surface of stem 128, to stretch the flexible material radially outward to an expanded condition.

As seen in FIG. 15, when used in connection with surgical stapling apparatus 10, drapes 140a, 140b function to maintain and hold the proximal and distal inverted flaps of the tissue "T" away from each other thereby providing a clear line of site from ports 128b formed in stem 128 and the staple line "S" of anastomosis site "A".

With continued reference to FIG. 15, use of the wound treatment material dispersion system of FIGS. 13 and 14, in connection with surgical stapling apparatus 10, is shown and described. In operation, the distal tissue "T" is sutured to stem 128 of anvil member 126 by a purse-string suture "P" at a location wherein the purse-string suture "P" is positioned distally of first drape 140a and, in particular, distally of outer radial edge 141a thereof. The proximal tissue "T" is sutured to stem 128 of anvil member 126 or connection means 30 by a purse-string suture "P", preferably at a location proximal of outer radial edge 141b of drape 140b.

With tissues "T" sutured to stem 128 and/or connection means 30, drapes 140a, 140b are deployed, as described above, in order for outer radial edge 141a, 141b to radially expand. Anvil member 126 is then approximated toward staple pusher member 22 so as to approximate distal and proximal tissue "T". Once again, as described above, drapes 140a, 140b hold the distal and proximal tissues "T", in the vicinity of purse-string sutures "P", separate from one another thereby providing a clear line of site between ports 128b of stem 128 and staple line "S".

Once the proper or desired distance is set between anvil member 126 and staple pusher member 22, interlock means 32 (see FIG. 1) may be released and actuating handles 14 may be pivoted to fire surgical stapling apparatus 10 and drive the staples through the tissue against anvil member 126 to complete the circular anastomosis of tissues "T". Either prior to, during or after the firing of surgical stapling apparatus 10, wound treatment material "W" is dispensed from anvil member 126, in any of the methods described herein above or herein below, to coat the staple line "S" to thereby reduce the occurrences of leaking and/or bleeding.

In particular, wound treatment material "W" is ejected from ports 128b of stem 128. For example, the wound treatment material "W" may be retained in an ampoule (not shown), which is ruptured to release the wound treatment material "W" contained therein, in a manner similar to that disclosed above with regard to FIGS. 4-8. It is further envisioned, for example, that a fluid conduit (not shown) may be provided which may deliver the wound treatment material "W" to ports 128b to be dispensed therefrom.

Drapes 140a, 140b allow for wound treatment material "W" to be dispensed from stem 128 of anvil member 126 to a target location (e.g., the staple line "E") and substantially prevent the application or spreading of wound treatment material "W" to unintended sections of body tissue.

Figure 16:
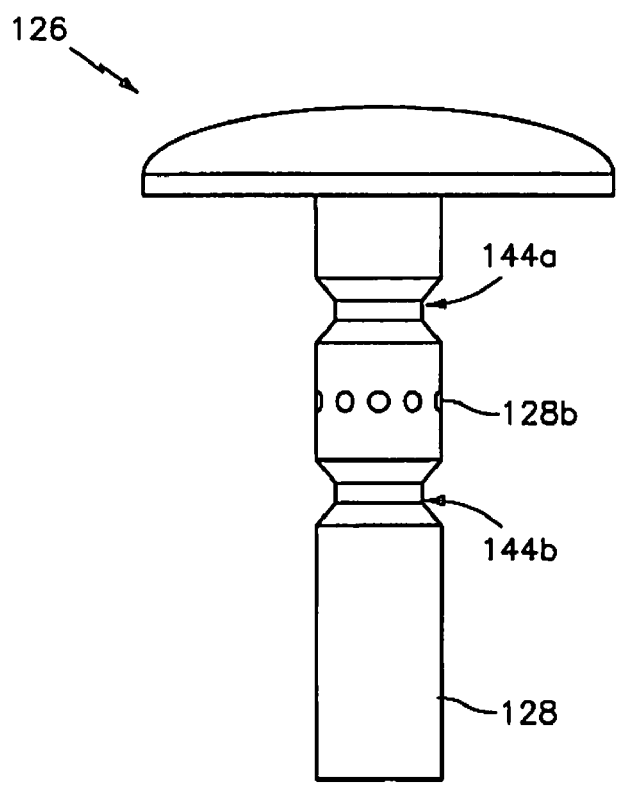
FIG. 16 is a side elevational view of yet another embodiment of the anvil member of FIGS. 4-6.

As seen in FIG. 16, stem 128 of anvil member 126 may include a first annular groove 144a formed distally of ports 128b and a second annular groove 144b formed proximally of ports 128b. In this manner, in use, the distal tissue "T" to be anastomosed is purse-string sutured to stem 128 such that the distal tissue "T" is positioned within first annular groove 144a. Additionally, the proximal tissue "T" to be anastomosed is purse-string sutured to stem 128 such that the proximal tissue "T" is positioned within second annular groove 144b.

In this manner, when anvil member 126 is approximated toward staple pusher member 22 and the distal and proximal tissues "T" are pinched therebetween along the staple line, grooves 144a, 144b maintain a portion of the distal and proximal tissue "T" (i.e., the portion of the tissue "T" between the staple line and grooves 144a, 144b) separate from one another thus maintaining a clear line of site between ports 128b and the staple line. In this manner, as wound treatment material "W" is dispensed from ports 128b of stem 128, the wound treatment material "W" may enter and contact the tissues "T" along the staple line.

Figure 17:
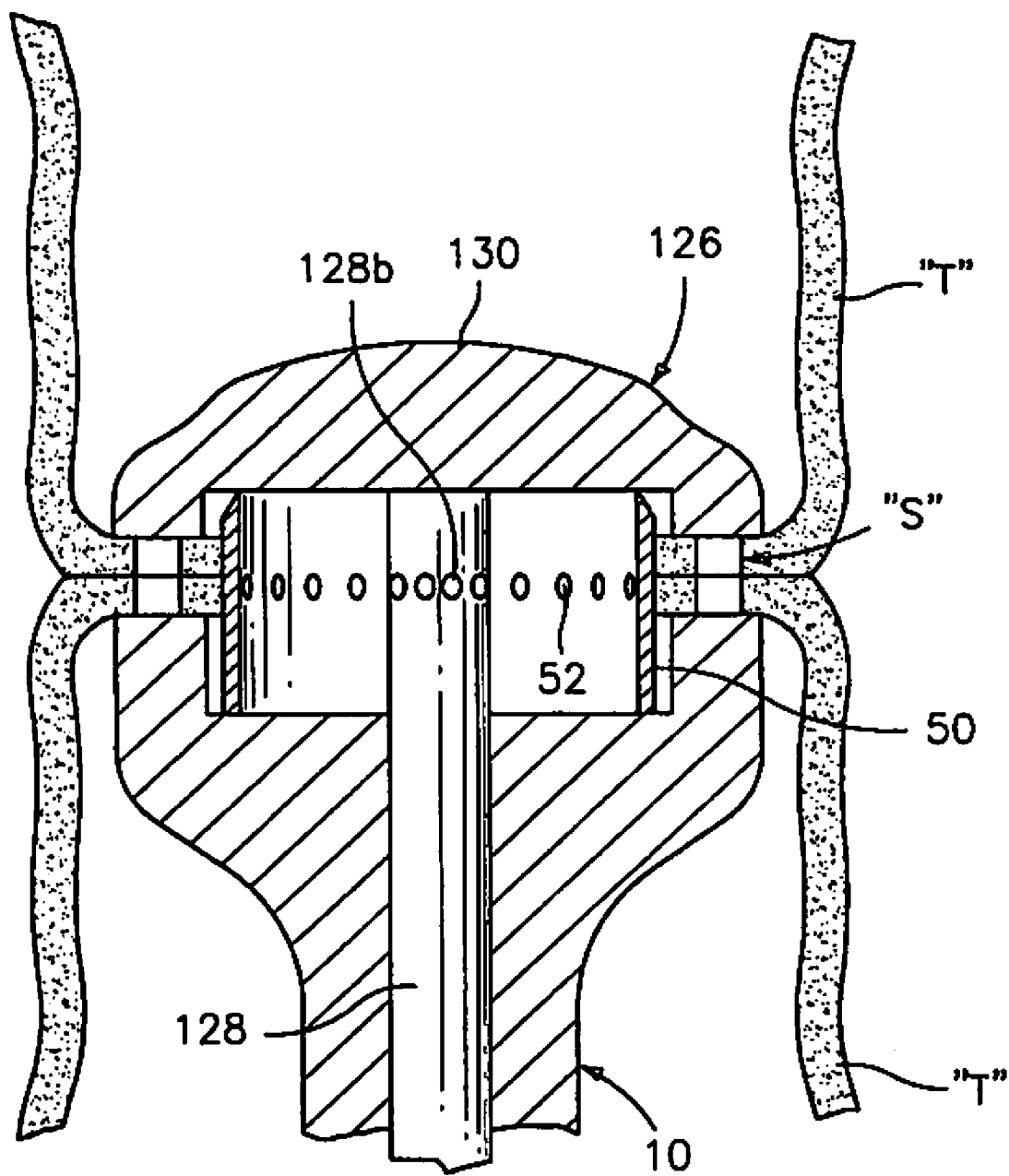
FIG. 17 is a schematic longitudinal cross-sectional view of the surgical stapling apparatus including an annular knife according to the present disclosure, showing the surgical stapling apparatus in a post fired condition.

Turning now to FIG. 17, in an alternate embodiment, if the wound treatment material "W" is to be applied to the tissues "T" along the staple line, following firing and before opening surgical stapler 10, it is envisioned and contemplated that the annular knife 50 of surgical stapling apparatus 10 be provided with a plurality of opening or apertures 52 formed therein. Preferably, when annular knife 50 is in an advanced position, apertures 52 will substantially radially align with ports 128b of stem 128 and with the staple line of the anastomosis. Accordingly, following firing of surgical stapling apparatus 10, the wound treatment material "W" may be dispensed from ports 128b of stem 128 and pass through apertures 52 of annular knife 50 in order to contact and coat the staple line.

Turning now to FIGS. 18-21, a wound treatment dispersion system, according to a further embodiment of the present disclosure, is shown and described. The dispersion system of FIGS. 18-21 includes an anvil member 226 which is connectable to connection means 30 of surgical stapling apparatus 10.

Figure 18:
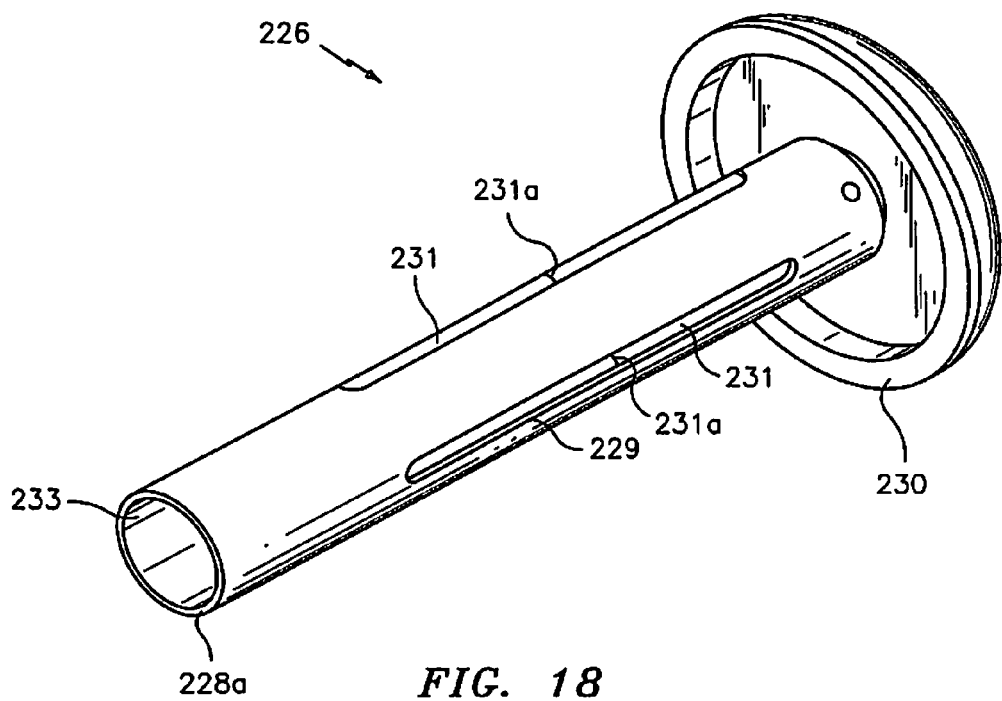
FIG. 18 is a perspective view of an anvil member according to an alternate embodiment of the present disclosure while in a first condition.
Figure 19:
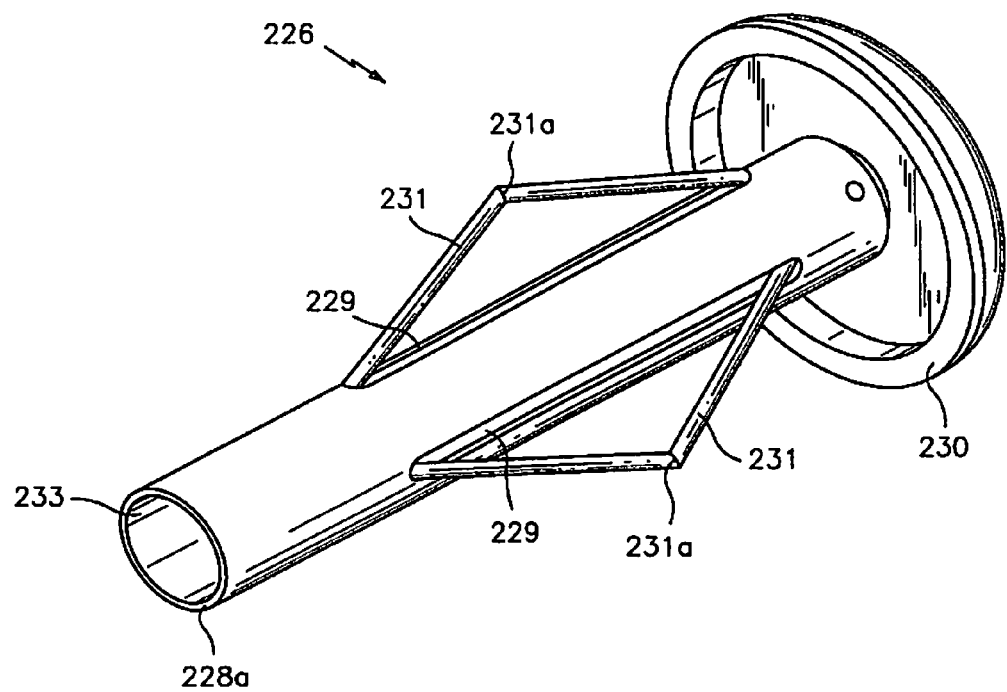
FIG. 19 is a perspective view of the anvil member of FIG. 18 while in a second condition.

As seen in FIGS. 18 and 19, anvil member 226 includes a hollow tubular stem 228 having an open proximal end 228a, and an anvil head 230 operatively connected to a distal end of stem 228. Stem 228 includes at least one, and in certain embodiments, a plurality of longitudinally oriented slots or elongate windows 229 formed therein, around the circumference of stem 228. Anvil member 226 further includes a flexible tubular member 231 operatively disposed within and deployable from each window 229: Stem 228 defines a lumen 233 therethrough which is in fluid communication with each tubular member 231 (see FIGS. 20 and 21).

As seen in FIG. 18, anvil member 226 has a first condition wherein each tubular member 231 is in an undeployed condition wherein each tubular member 231 is disposed within a respective window 229. As seen in FIG. 19, anvil member 226 has a second condition wherein each tubular member 231 is in a deployed condition wherein each tubular member 231 is bent along an elbow, flex point or region of weakness 231a in such a manner that each tubular member 231 extends radially outward from windows 229.

Each tubular member 231 is capable of retaining, carrying and/or transmitting wound treatment material "W" therein or therethrough. As will be described in greater detail below, in use, as anvil member 226 is moved from the first condition to the second condition, tubular members 231 are deployed. The deployment of tubular members 231 causes tubular members 231 to develop an opening, fissure or crack along flex point 231a. In this manner, wound treatment material "W" may be dispensed therefrom.

Flex point 231a is formed along tubular members 231 at a location such that when anvil member 226 is in the second condition and tubular members 231 are deployed, flex points 231a are located in close proximity to or in axial and radial alignment with anastomosis site "A". In this manner, when wound treatment material "W" is dispersed from tubular members 231, the wound treatment material "W" is dispersed into and/or onto anastomosis site "A".

Figure 20:
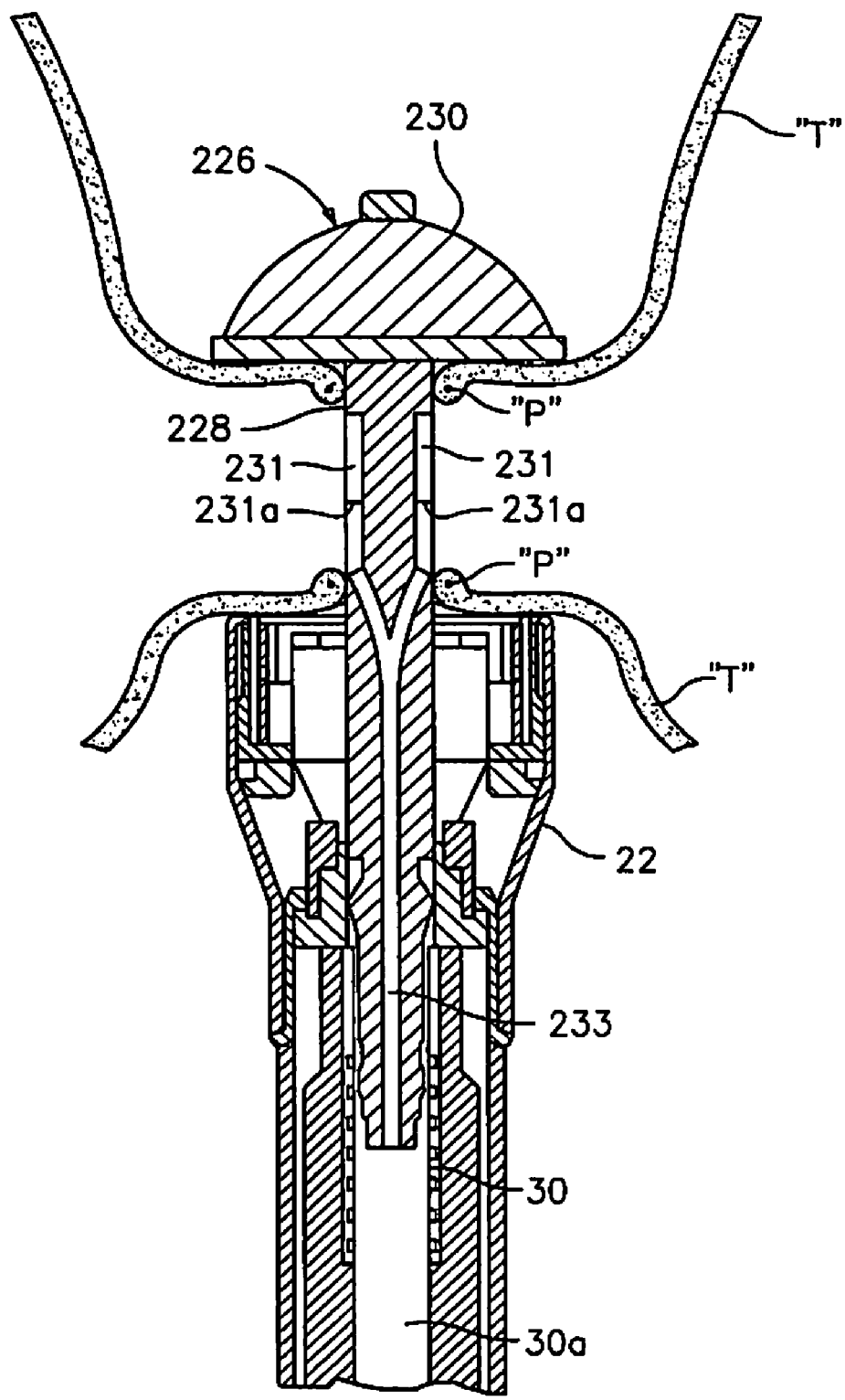
FIG. 20 is a longitudinal cross-sectional view of the distal end of a surgical stapling apparatus having a wound treatment material dispersion system, including the anvil member of FIGS. 18 and 19, operatively associated therewith, wherein the surgical stapling apparatus is in a first position within an operative site.
Figure 21:
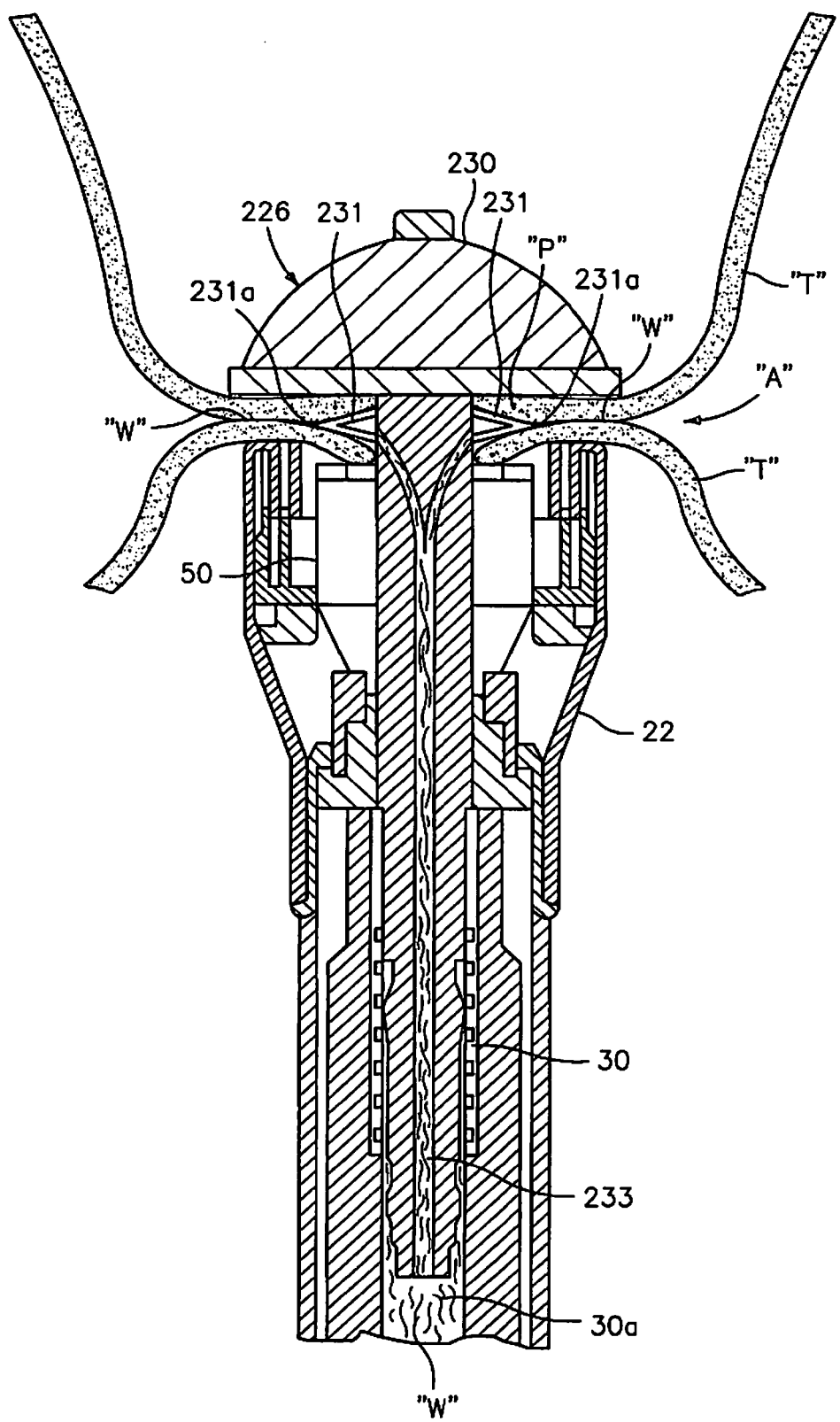
FIG. 21 is a longitudinal cross-sectional view of the distal end of the surgical stapling apparatus of FIG. 21, wherein the surgical stapling apparatus is in a second position in the operative site.

Turning now to FIGS. 20 and 21, use of the wound treatment material dispersion system of FIGS. 18 and 19, in connection with surgical stapling apparatus 10, is shown and described. In operation, anvil member 226 is introduced into one side of the anastomosis according to any known technique. The tissue "T" is then purse string sutured to stem 228 such that purse string suture "P" is located distally of windows 229. Stem 228 of anvil member 226 may then be operatively connected to connection means 30 such that lumen 30a of connection means 30 is in fluid communication with lumen 233 of stem 228 of anvil member 226. With anvil member 226 connected to the distal end of surgical stapling apparatus 10, the surgical procedure is continued as described above.

Anvil member 226 is then approximated toward staple pusher member 22 by rotating grip member 18 (see FIG. 1). As grip member 18 is rotated, anvil member 226 is drawn into position adjacent staple pusher member 22 to locate the ends of tissue "T" therebetween. Simultaneously therewith, as anvil member 226 is drawn towards staple pusher member 22, tubular member 231 of the wound treatment material dispersion system are deployed such that flex points 231a are located in close proximity to or in axial and radial alignment with anastomosis site "A".

As tubular members 231 are deployed, tubular members 231 will develop a crack or fissure (not shown) along flex points 231a. In this manner, wound treatment material "W" may be dispensed onto anastomosis site "A". Anvil member 226 is constructed in such a manner that when tubular members 231 are in the deployed condition, flex points 231a do not extend radially beyond annular knife blade 50.

Once the wound treatment material "W" has been dispensed onto tissue "T" and once tissue "T" has been clamped between anvil member 226 and staple pusher member 22, interlock means 32 (see FIG. 1) may be released and actuating handles 14 may be pivoted to drive the staples through tissue "T" and against head 230 of anvil member 226 to complete the circular anastomosis of the tubular organ.

Figure 22:
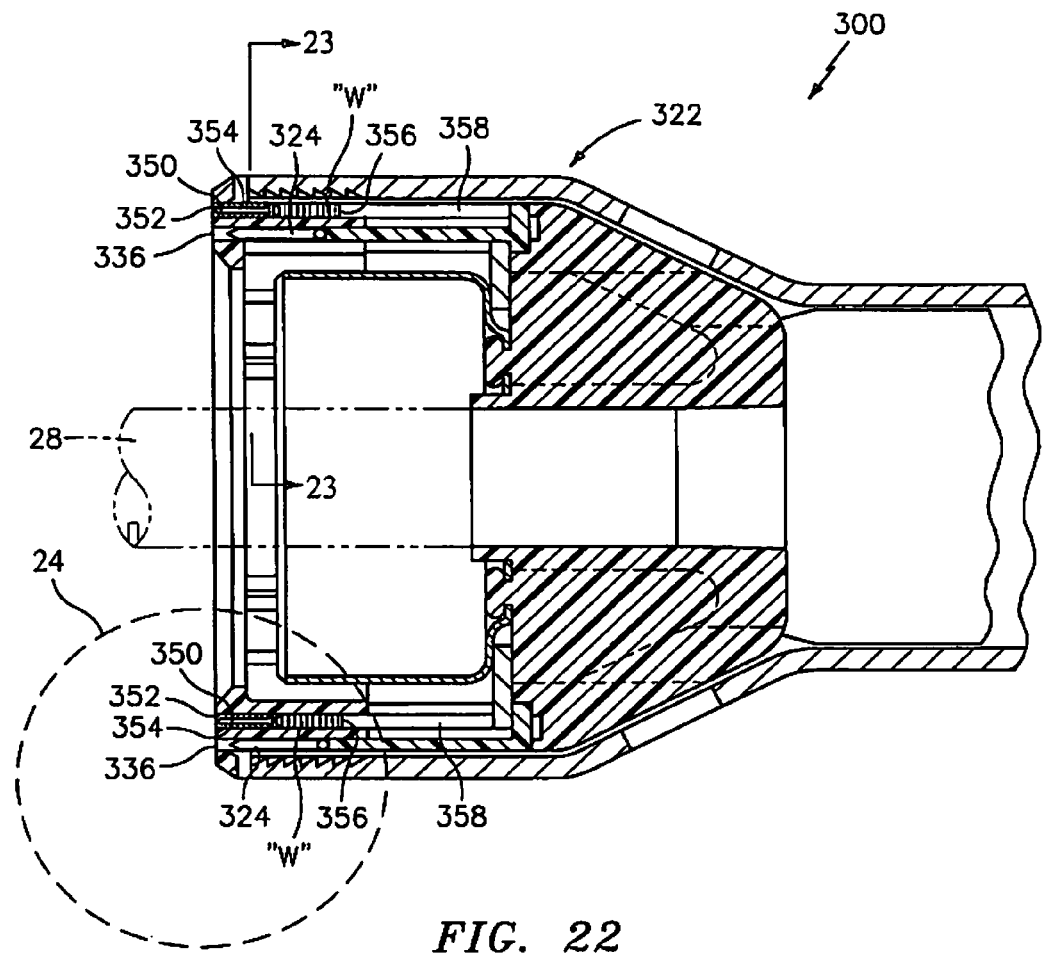
FIG. 22 is an enlarged longitudinal cross-sectional view of a surgical stapling apparatus according to an alternate embodiment of the present disclosure.
Figure 23:
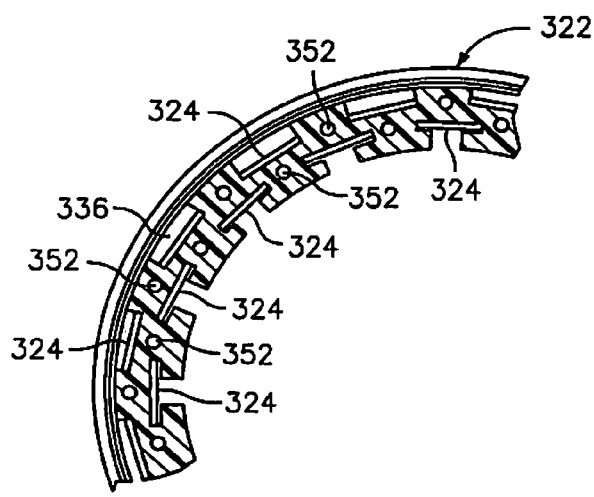
FIG. 23 is an enlarged partial sectional view taken along lines 23-23 of FIG. 22.
Figure 24:
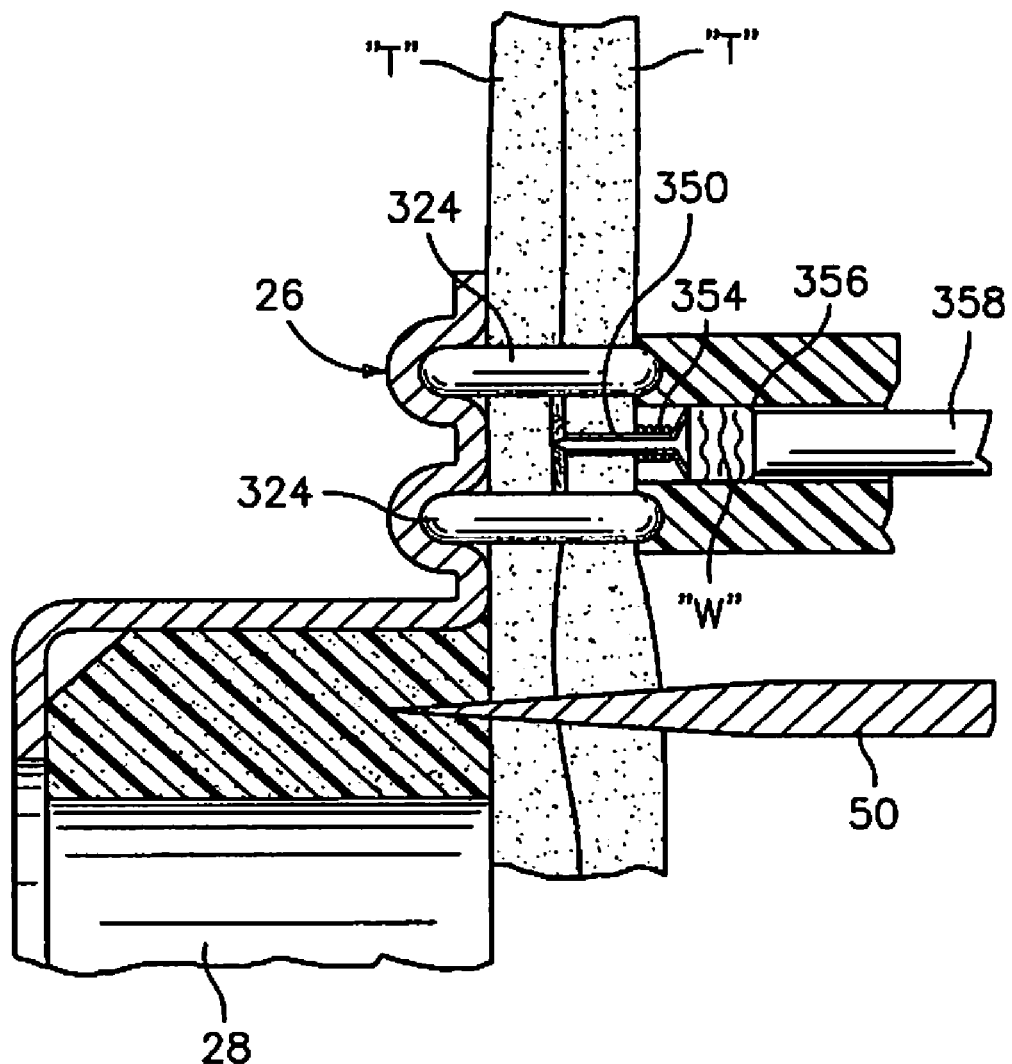
FIG. 24 is an enlarged view of the area indicated as 24 in FIG. 22.

Turning now to FIGS. 22-24, a surgical stapling apparatus in accordance with an alternate embodiment of the present disclosure is shown generally as 300. Surgical stapling apparatus 300 is substantially similar to surgical stapling apparatus 10 and thus will only be discussed in detail to the extent necessary to identify differences in construction and operation.

As seen in FIGS. 22-24, surgical stapling apparatus 300 includes a wound treatment material dispersion system configured and adapted to dispense wound treatment material "W" to a target surgical site. The wound treatment material dispersion system of FIGS. 22-24 includes at least one annular array, in certain embodiments, two annular arrays, of deployable needles 350 positioned within needle receiving slots 352 formed in a distal end of staple pusher member 322. Each needle 350 is biased to a retracted position within its respective needle receiving slot 352 by a biasing member or spring 354 positioned about each needle 350 and disposed between an inner distal surface 322a of staple pusher member 322 and a flange 350a formed at a proximal end of each needle 350.

A quantity of wound treatment material "W" is provided within each needle receiving slot 352, at a location proximal of needle 350. A plurality of rigid, semi-rigid or flexible containers, here shown as semi-rigid or flexible capsules 356, containing wound treatment material "W" may be provided, one each, within needle receiving slots 352. Each capsule 356 encloses, encapsulates and/or includes a quantity of wound treatment material therein.

In operation, as seen in FIGS. 22 and 24, with tissue "T" clamped between anvil member 330 and staple pusher member 322, actuation of handle members 14 (see FIG. 1), results in distal advancement of fingers 358 through needle receiving slots 352. Fingers 358 push capsules 356 (containing wound treatment material "W" therein) in a distal direction against a proximal end of needles 350 resulting in the deployment of needles 350 out of needle receiving slots 352. Simultaneously therewith or immediately thereafter, needles 350 are deployed (e.g., distally advanced) to penetrate at least one layer of tissue "T".

Once needles 350 are fully deployed, further actuation of handle members 14 results in fingers 358 exerting a compressive force on capsules 356 to cause capsules 356 to rupture and dispense wound treatment material "W" into respective needle receiving slot 352. With capsules 356 ruptured, continued actuation of handle members 14 and distal advancement of fingers 358 results in the expulsion or dispensing of wound treatment material "W" out through and/or about needles 350.

Following firing of surgical stapling apparatus 300, handle members 14 are released to move fingers 358 in a proximal direction thus allowing needles 350 to retract into slots 352 as a result of the biasing force created by springs 354.

In this manner, the annular array of staples 324 provide the necessary retraining force to mechanically hold the adjacent layers of tissue "T" secured to one another during the healing process while a suitable wound treatment material "W" fills the gaps between adjacent staples 324 in a particular annular array of staples 324.

It is contemplated and within the scope of the present disclosure to provide a surgical stapling apparatus containing no staples whatsoever. As such, the anastomosis and the joining of tissue "T" would be accomplished by the adherence of tissues "T" to one another by wound treatment material "W".

It is further envisioned and contemplated that surgical stapling apparatus 300 may be configured to drive needles 350 through both layers of tissue "T". As such, surgical stapling apparatus 300 may also be configured to dispense wound treatment material "W" through needles 350 as needles 350 are being retracted into staple pusher member 322. In this manner, wound treatment material "W" may span across both layers of tissue "T" on either side of the anastomosis.

Turning now to FIGS. 25-28, a splash guard 400 is shown and will be described. Splash guard 400 may be used with any of the surgical apparatus' disclosed above. Splash guard 400 is intended to prevent leakage of wound treatment material from the outer surface of the anastomosis. As will be described in greater detail below, in use, splash guard 400 creates a barrier around the periphery of the anastomosis which inhibits and/or prevents leakage of wound treatment material "W" to other parts of the anatomy by localizing the wound treatment material "W" to the site of the anastomosis. Additionally, splash guard 400 may help to reduce to occurrence of bleeding at or from the site of the anastomosis.

Figure 25:
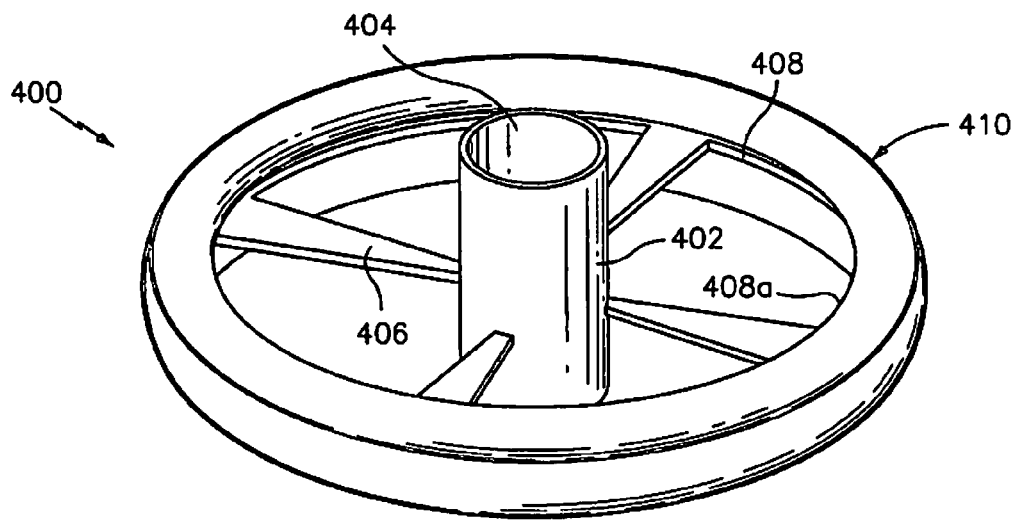
FIG. 25 is a perspective view of a splash guard for use with the surgical stapling apparatus disclosed herein.
Figure 26:
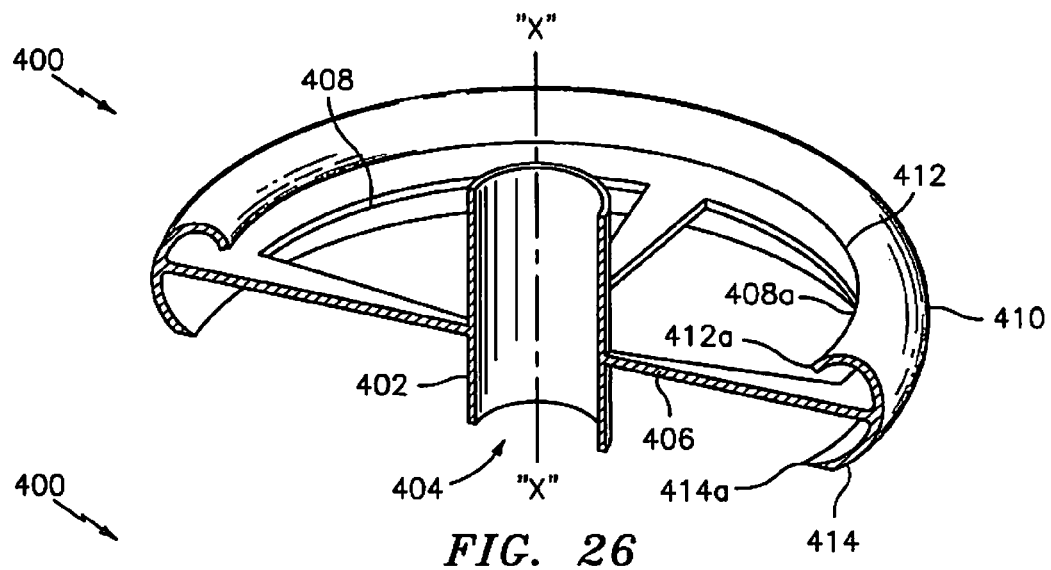
FIG. 26 is a perspective longitudinal cross-sectional view of the splash guard of FIG. 25.
Figure 27:
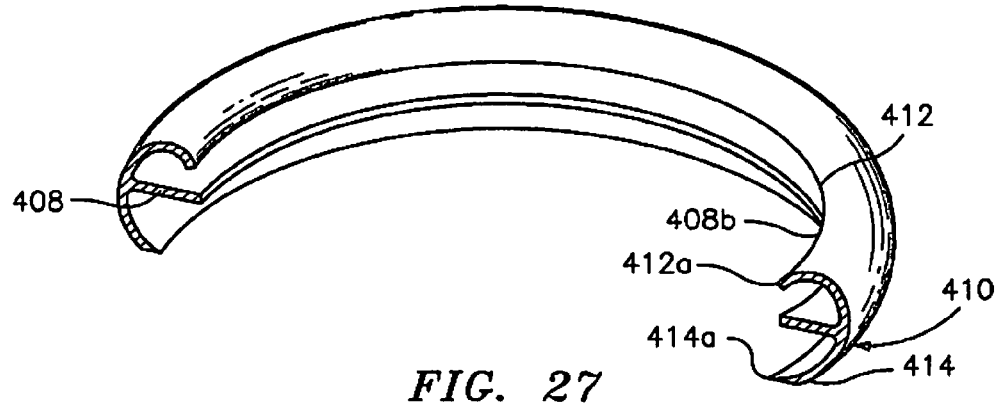
FIG. 27 is a perspective longitudinal cross-sectional view of the splash guard of FIG. 25 illustrating the splash guard following firing of the surgical stapling apparatus.

As seen in FIGS. 25-27, splash guard 400 includes a central hub 402 including a central lumen 404 and defining a central longitudinal axis "X". Splash guard 400 further includes at least one spoke 406 extending radially outward from central hub 402. As seen in FIG. 25, splash guard 400 may include four spokes 406 extending from central hub 402 wherein spokes 406 are equally spaced from one another. However, it is envisioned and within the scope of the present disclosure, that any number of spokes may be provided and which spokes may be spaced any distance from one another. It is further envisioned that spokes 406 may be replaced by an annular disc (not shown) extending radially and/or orthogonally from central hub 402.

Splash guard 400 further includes an annular flange 408 interconnecting the outer or distal ends of spokes 406. Annular flange 408 provides support for spokes 406, as well as, and as will be described in greater detail below, a surface through which the staples of the surgical stapling apparatus are fired.

Splash guard 400 further includes an annular cuff 410 integrally connected to an outer terminal edge of annular flange 408. Cuff 410 includes an upper lip 412 extending distally from a first or distal surface of annular flange 408 and a lower lip 414 extending proximally from a second or proximal surface of annular flange 408. Preferably, upper lip 412 terminates in an upper annular rim 412a having a central diameter which is less than an outer diameter of annular flange 408. Likewise, lower lip 414 preferably terminates in a lower annular rim 414a having a central diameter which is less than an outer diameter of annular flange 408. In this manner, as seen in FIG. 26, cuff 410 has a C-shaped or concave cross-sectional profile.

Preferably, at least a portion of splash guard 400 and, more preferably, the entirety of splash guard 400 is fabricated from a semi-rigid, bio-absorbable material. In this manner, those portions of splash guard 400 left at the anastomosis site, following the surgical stapling procedure, will help to prevent the occurrences of stricture at or near the site of the anastomosis.

Figure 28:
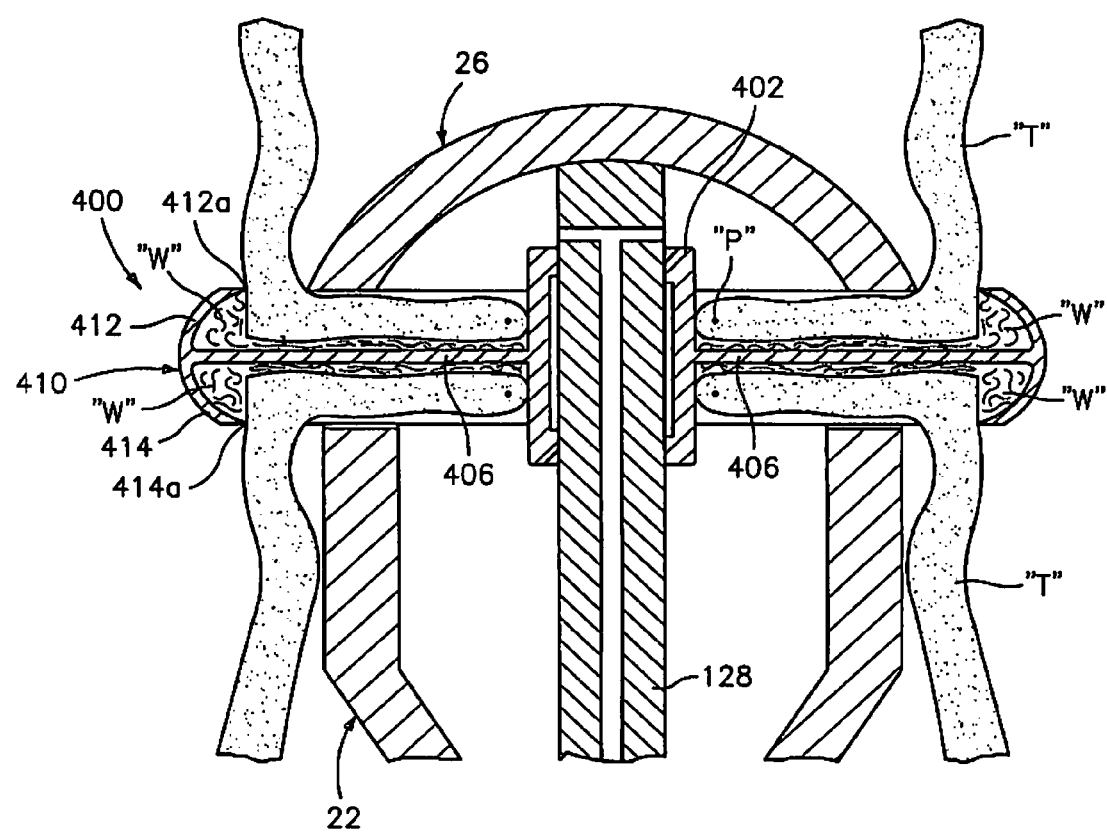
FIG. 28 is a schematic, longitudinal cross-sectional view of the splash guard of FIGS. 25-27, in position at a target surgical site, the surgical stapling apparatus being shown in phantom.

Turning now to FIG. 28, an exemplary method of using splash guard 400, in combination with any one of the surgical stapling apparatus' described above, will now be shown and described. According to one method of operation, the ends of the organ to be joined (e.g., the tissue "T") are secured over staple pusher member 22 and anvil member 26 by a purse string suture "P" prior to approximation of anvil member 26 in relation to staple pusher member 22.

With tissue "T" sutured to staple pusher member 22 and anvil member 26, splash guard 400 is positioned on stem 128 of anvil member 26 such that stem 128 extends through lumen 404 of central hub 402. Preferably, splash guard 400 is dimensioned so that upper and lower lips 412, 414 of cuff 410 are disposed radially outward of radially outer-most annular staple line of staple pusher member 22. Additionally, splash guard 400 is dimensioned so that an inner annular terminal edge 408a (see FIGS. 25 and 26) of annular flange 408 is disposed radially inward of the annular knife cut line.

With splash guard 400 positioned on stem 128 of anvil member 26, stem 128 of anvil member is operatively connected to the connection means (not shown) of staple pusher member 22. Anvil member 26 is then approximated towards staple pusher member 22 in the manner described above. Prior to, during or after approximation of anvil member 26 toward staple pusher member 26, it is envisioned that wound treatment material "W" may be sprayed or dispensed onto tissue "T" as described above (e.g., from ports formed in the stem of anvil member 26). Desirably, sufficient wound treatment material "W" is sprayed onto tissue "T" to sufficiently cover that portion of tissue "T" to be anastomosed. It is envisioned that central hub 402 may include at least one aperture (not shown) formed therein to enable wound treatment material "W" to be dispensed through and radially outward from central hub 402.

Desirably, splash guard 400 is dimensioned so that rims 412a, 414a of upper and lower lips 412, 414 of cuff 410 are in contact with an outer surface of tissue "T". As such, cuff 410 will act as a barrier to help localize any fluid (i.e., wound treatment material "W", blood, etc.) at the outside of the anastomosis site.

As anvil member 26 is approximated towards and clamped against staple pusher member 22, wound treatment material "W" will tend to be squeezed radially inward and radially outward of the anastomosis site. As discussed above, cuff 410 of splash guard 400 acts as a barrier to prevent wound treatment material "W" from spreading through the operative site.

With wound treatment material "W" dispersed over tissue "T" and with splash guard 400 positioned on stem 128 of anvil member 26, stem 128 of anvil member 26 is operatively connected to connection means 30 located within staple pusher member 22. With anvil member 126 connected to the distal end of surgical stapling apparatus 10, the surgical procedure is continued as described above. In particular, the surgical stapling apparatus may be fired by releasing interlock means 32 (see FIG. 1) and actuating handles 14 may be pivoted to drive the staples through tissue "T", through annular flange 408, and against anvil member 26 to complete the circular anastomosis of tissue "T". Additionally, as the surgical stapling apparatus is being fired, the annular knife is driven through tissue "T" and annular flange 408 of splash guard 400 to thereby sever that portion of tissue "T" and that portion of annular flange 408 disposed radially inward of the annular knife blade. In so doing, central hub 402 and spokes 406 are separated from the remainder of splash guard 400. Accordingly, as seen in FIG. 27, the annular knife blade creates a knife cut line 408b in annular flange 408.

Figure 29:
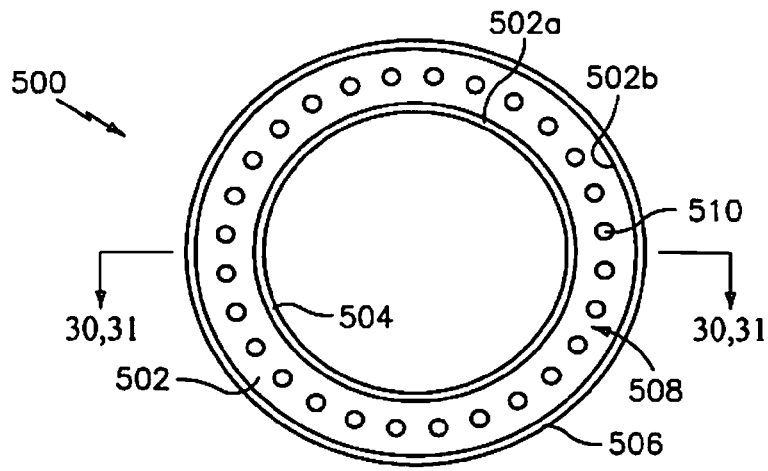
FIG. 29 is a top plan view of a wound treatment material dispersion system according to a further embodiment of the present disclosure.
Figure 30:
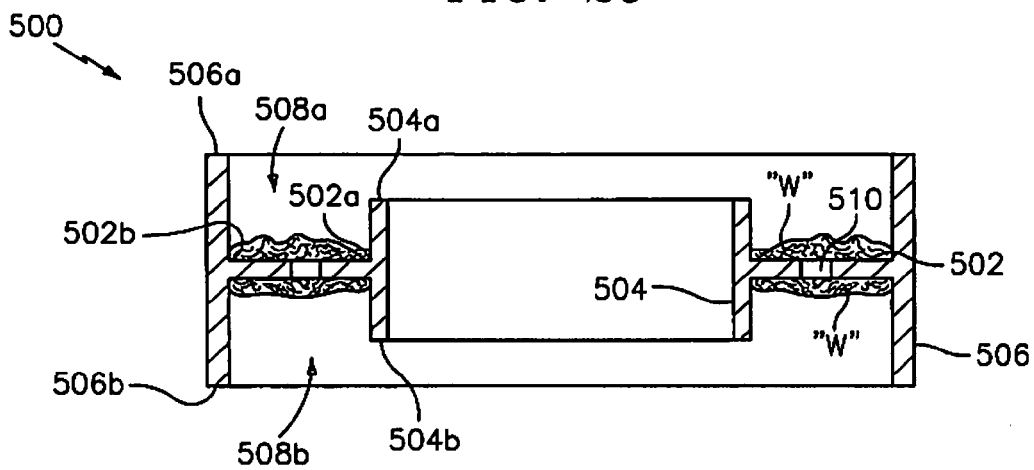
FIG. 30 is a cross-sectional view of the wound treatment material dispersion system of FIG. 29 as taken through 30-30 of FIG. 29.
Figure 31:
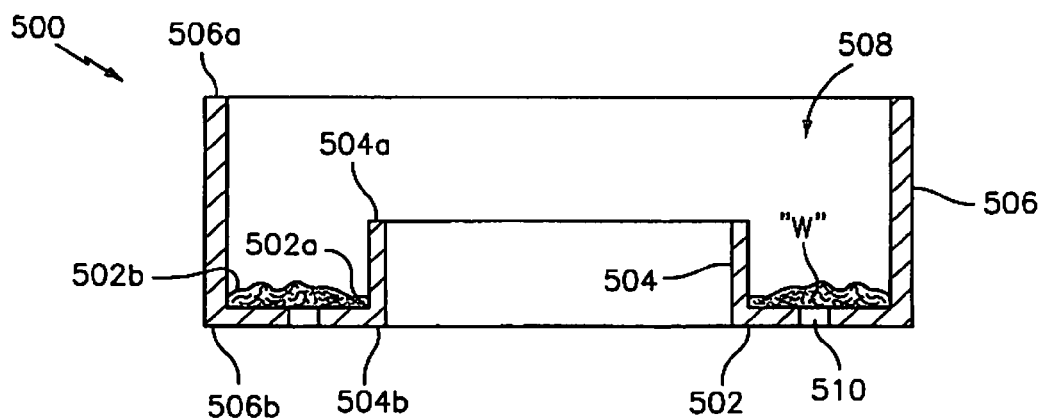
FIG. 31 is a cross-sectional view of a wound treatment material dispersion system according to another embodiment of the present disclosure as would be taken through 30-30 of FIG. 29.

Turning now to FIGS. 29-33, a wound treatment material dispersion system, according to another embodiment of the present disclosure is shown generally as 500. As seen in FIGS. 29-31, wound treatment material dispersion system 500 includes a ring or disc 502 defining an inner terminal edge 502a and an outer terminal edge 502b. Dispersion system 500 further includes at least one of an annular inner wall 504 integrally connected to inner terminal edge 502a of disc 502 and an annular outer wall 506 integrally connected to outer terminal edge 502b of disc 502. Preferably, as seen in FIGS. 30 and 31, dispersion system 500 includes both an annular inner wall 504 and an annular outer wall 506.

Desirably, annular inner wall 504 and annular outer wall 506 are substantially orthogonal with respect to disc 502. In one embodiment, as seen in FIG. 30, disc 502 is positioned between an upper terminal edge 504a, 506a of inner and outer walls 504, 506, respectively, and a lower terminal edge 504b, 506b of inner and outer walls 504, 506, respectively. In this manner, dispersion system 500 defines a first or upper annular channel 508a and a second or lower annular channel 508b. Desirably, wound treatment material "W" is disposed or deposited within at least one of first and second annular channels 508a, 508b.

Additionally, as seen in FIG. 30, annular outer wall 506 preferably has a height which is greater than a height of annular inner wall 504. Alternatively, it is envisioned that the height of annular outer wall 506 may be substantially equal to or less than the height of annular inner wall 504.

As seen in FIG. 31, in another embodiment, disc 502 may be positioned either at upper terminal edges 504a, 506a of inner and outer walls 504, 506, respectively, or at lower terminal edges 504b, 506b of inner and outer walls 504, 506, respectively. In this manner, a single annular channel 508 is defined for retaining a quantity of wound treatment material "W" therein.

As seen in FIGS. 29-31, disc 502 is preferably provided with a series of opening or apertures 510 formed therein and preferably therearound. In this manner, wound treatment material "W" is free to and/or capable of flowing to a side of disc 502 opposite the side on which wound treatment material "W" is deposited.

Preferably, at least a portion of dispersion system 500 and, more preferably, the entirety of dispersion system 500, is fabricated from a semi-rigid, bio-absorbable material. In this manner, those portions of dispersion system 500 left at the anastomosis site, following the surgical stapling procedure, will help to prevent the occurrences of stricture at or near the site of the anastomosis.

As seen in FIGS. 29-31, annular inner wall 504 of dispersion system 500 defines a central aperture 510. Preferably, as will be shown in FIGS. 32 and 33, dispersion system 500 is dimensioned such that when dispersion system 500 is positioned on stem 28 of anvil member 26, annular outer wall 506 is positioned radially outward of an outer radial terminal edge of anvil member 26 and inner terminal edge 502a of disc 502 terminates radially inward of a radially inner-most staple line (not shown).

Figure 32:
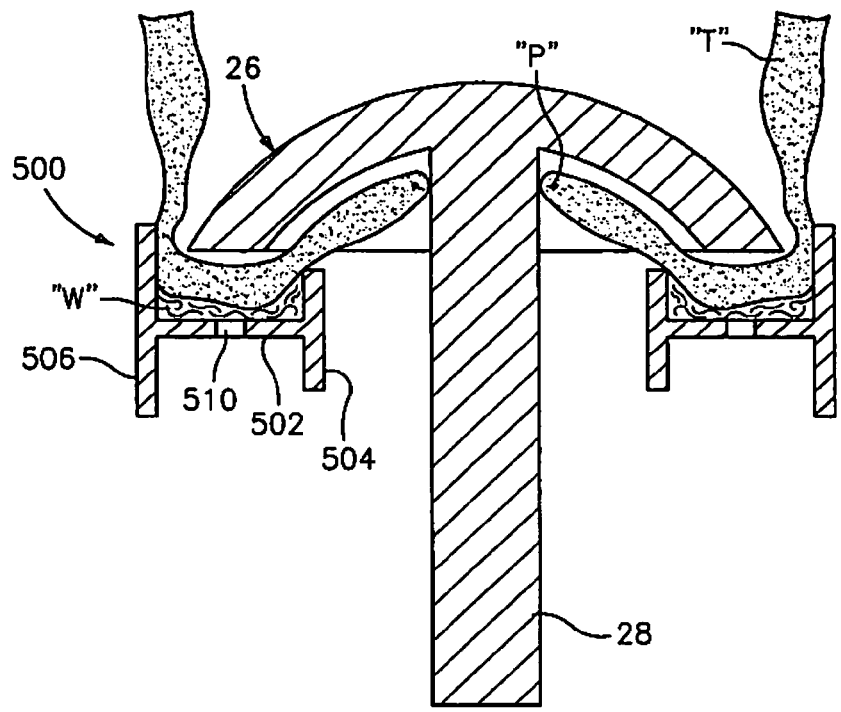
FIG. 32 is a longitudinal cross-sectional view of a surgical stapling apparatus illustrating a method of using the wound treatment material dispersion system of FIGS. 29 and 30 in conjunction therewith.
Figure 33:
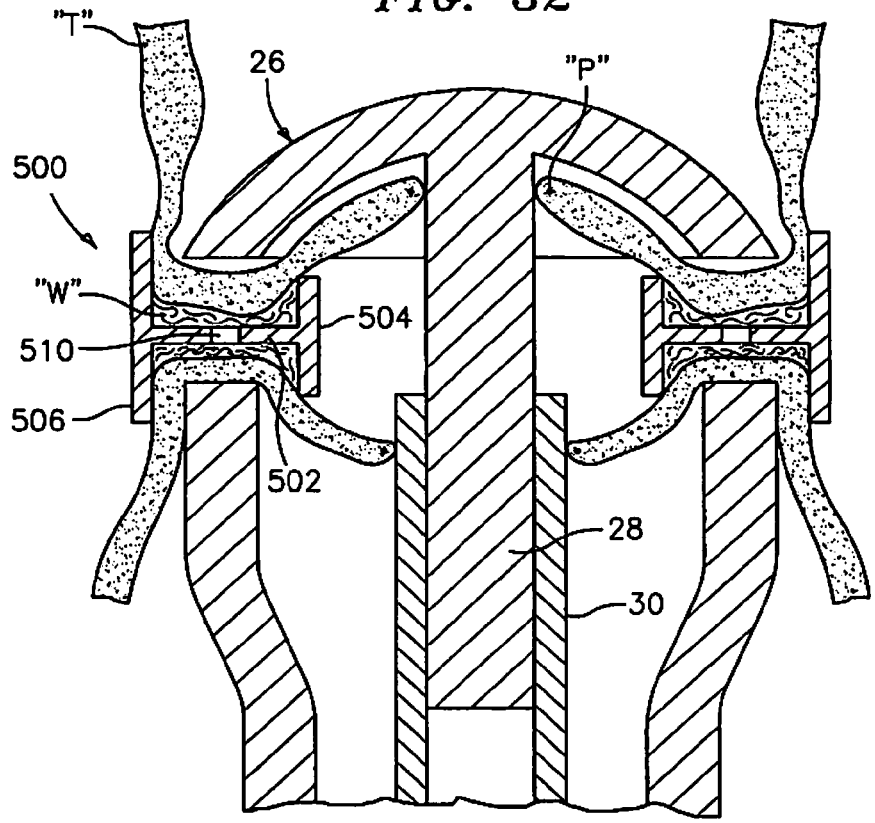
FIG. 33 is a longitudinal cross-sectional view of a surgical stapling apparatus illustrating an alternate method of using the wound treatment material dispersion system of FIGS. 29 and 30 in conjunction therewith.

Turning now to FIGS. 32 and 33, exemplary methods of using dispersion system 500, in connection with a surgical stapling apparatus 10, will be shown and described. As seen in FIG. 32, with tissue "T" purse string sutured to stem 28 of anvil member 26, dispersion system 500, including a quantity of wound treatment material "W" disposed within one of annular channels 508a, 508b, is placed over stem 28 and brought into contact with tissue "T" in a manner so as bring wound treatment material "W" into contact with tissue "T". In so doing, wound treatment material "W" is transferred to tissue "T". With wound treatment material "W" transferred to tissue "T", dispersion system 500 may be removed and the surgical stapling process continued as described above.

Alternatively, as seen in FIG. 33, dispersion system 500 may be left in place against tissue "T" following the anastomosis procedure. In particular, with dispersion system 500 positioned on stem 28 of anvil member 26, stem 28 of anvil member 26 coupled to connection means 30 and anvil member 26 is approximated toward staple pusher member 22. In so doing, wound treatment material "W" is squeezed through or will spread through openings 510 to cover both layers of tissue "T" to be approximated. With dispersion system 500 so disposed, the surgical stapling process is continued as describe above in order to complete the anastomosis. According to the present procedure, dispersion system 500 will remain in position between the two adjacent layers of anastomosed tissue "T".

It is envisioned and within the scope of the present disclosure that would treatment material "W" may be a fluid, a solid or some combination of a fluid and a solid (e.g., foam). For example, wound treatment material "W" may be an expandable foamy fluid which may be injected, sprayed and/or otherwise dispersed or applied between two layers of tissue "T". The foam wound treatment material "W" may be an adhesive capable of holding the two layers of tissue "T" together until such time as normal tissue healing may occur.

The adhesive may be moisture activated, two-part reactive, or any other suitable biocompatible type adhesive. If a two-part reactive adhesive is used, the adhesive may be mixed or cured in a number of different manners. For example, the adhesive may be mixed or cured by 1) providing a first and/or a second part of the adhesive in micro-spheres which rupture upon application of pressure, vibration, shock or other suitable means; 2) the first part of adhesive being a foam and the other part of the adhesive being encapsulated in micro-spheres or the like; and 3) the first part of the adhesive is a foaming agent encapsulated in micro-spheres and which may be combined with a singe part adhesive, or with one or both parts of a two-part adhesive.

In use, as the bubble in the foam based adhesive collapses, direct contact between the surfaces of tissue "T" will occur and create an opportunity to tissue cells to grow and thereby bring about natural healing. Using an adhesive that is foam based helps to maintain the adhesive in the location in which it is applied and helps to maintain the adhesive in contact with tissue "T" until curing of the adhesive may commence.

Figure 34:
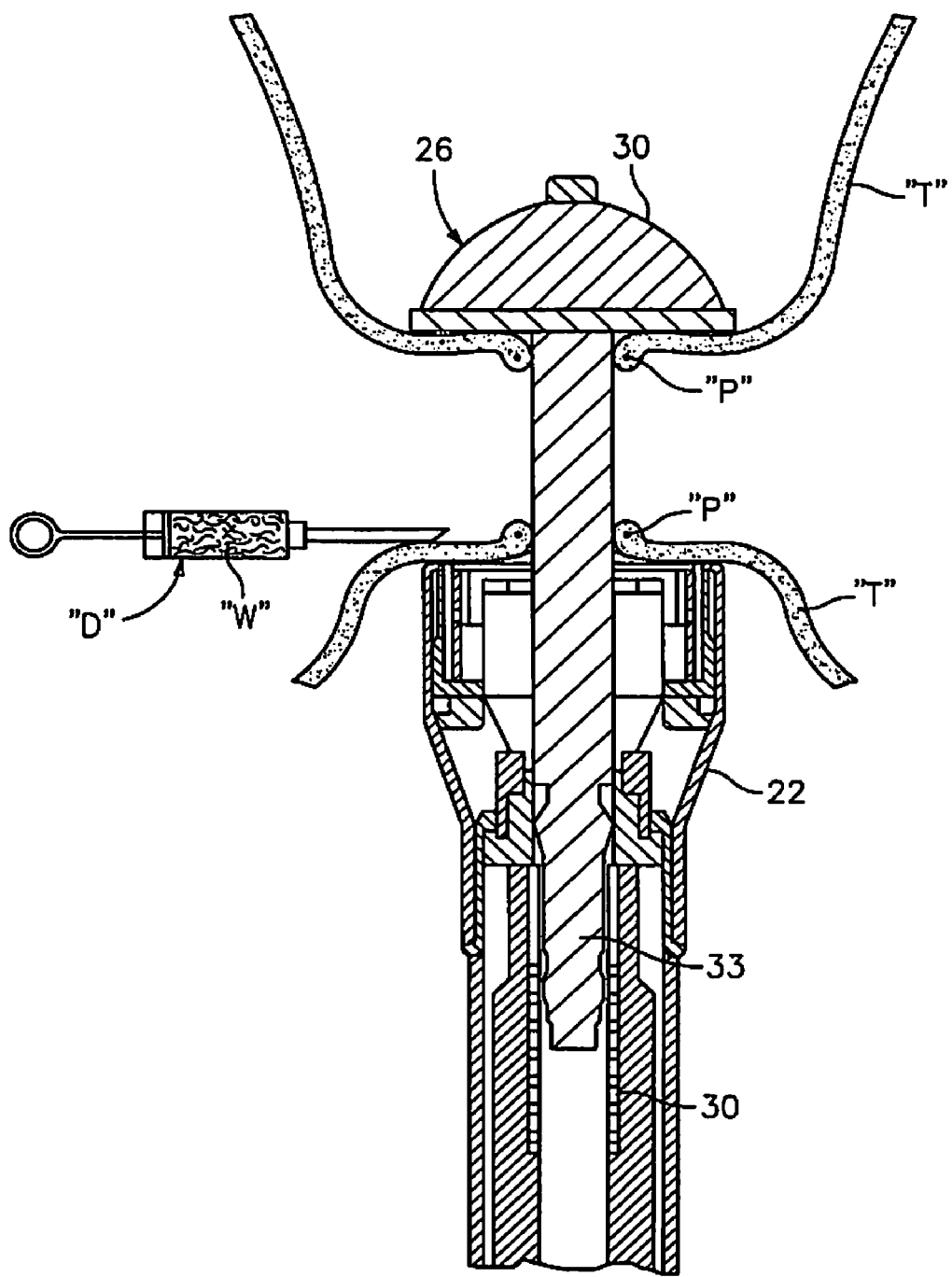
FIG. 34 is a longitudinal cross-sectional view of the distal end of a surgical stapling apparatus illustrating a step in a method of dispensing a wound treatment material to an anastomosis site.
Figure 35:
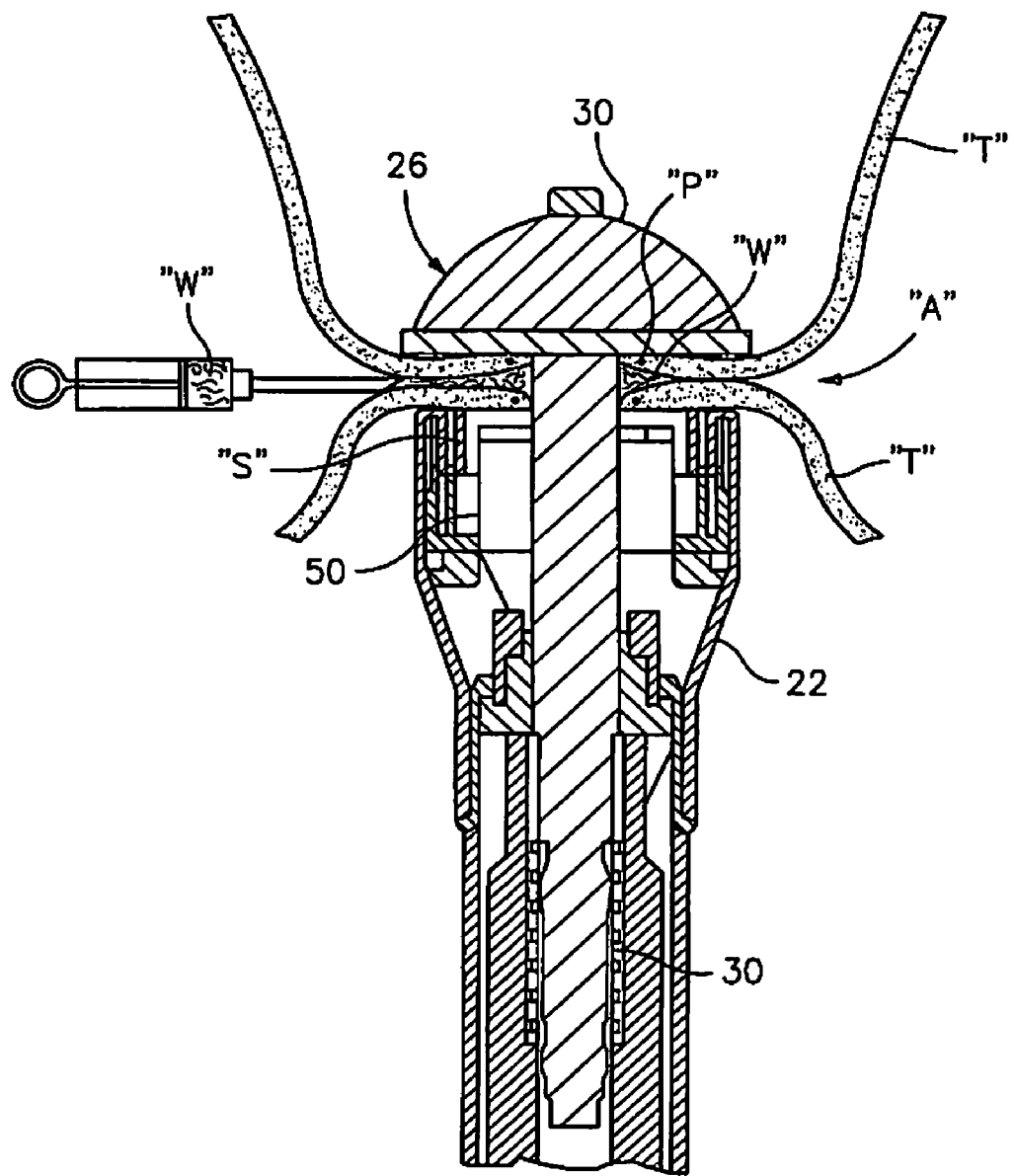
FIG. 35 is a longitudinal cross-sectional view of the distal end of the surgical stapling apparatus of FIG. 34 illustrating a further step in the method of dispensing a wound treatment material to an anastomosis site.

Turning now to FIGS. 34 and 35, an alternative method of dispensing wound treatment material "W" to anastomosis site "A" is shown and described. According to the method disclosed in FIGS. 34 and 35, the ends of the organ to be joined (e.g., the tissue "T") are secured over staple pusher member 22 and anvil member 26 by a purse string suture "P" prior to approximation of anvil member 26 in relation to staple pusher member 22.

With tissue "T" sutured to staple pusher member 22 and anvil member 26, stem 128 of anvil member 26, stem 128 of anvil member 26 is operatively connected to the connection means (not shown) of staple pusher member 22. Prior to approximation of anvil member 26 and staple pusher member 22, a tip, nozzle or distal end of a fluid dispensing or delivery device "D" (e.g., a syringe, a blunt hypodermic needle, etc.) is placed between the layers of tissue "T" to be anastomosed.

With the distal tip of dispensing device "D" so positioned, anvil member 26 is slowly approximated towards staple pusher member 22 in the manner described above, thereby trapping the distal end of dispensing device "D" therebetween. As dispensing device "D" is withdrawn from the operative site and the distal tip thereof withdrawn from between the layers of tissue "T", wound treatment material "W" is dispensed and/or otherwise injected therebetween.

It is envisioned and within the scope of the present disclosure that one or more rows of staples "S" may be fired radially inward of, radially outward of, or on both sides of the distal tip of dispensing device "D", either before, during or after the wound treatment material "W" is dispensed between the layers of tissue "T". Desirably, sufficient wound treatment material "W" is dispensed between the layers of tissue "T" to sufficiently cover that portion of tissue "T" to be anastomosed.

After a period of time, direct contact between the layers of tissue "T" will create an opportunity for tissue cells to grow therebetween, bringing about natural healing. Simultaneously therewith, the staples will begin to dissolve and be absorbed into the body as the natural healing process supplies greater strength and security to the anastomosis site.

While it is typical for the surgical staples to be applied in an orientation which is tangential to the annular staple line, it is envisioned and within the scope of the present disclosure for the surgical staples to be applied in an orientation which is orthogonal to or perpendicular to the annular staple line. In this manner, the staples would be better able to straddle the distal tip of dispensing device "D" and thereby better maintain the distal tip thereof in a straight line during withdrawal of the distal tip from between the layers of tissue "T".

It is further envisioned that the surgical staples may be closed and/or formed into a D-shape instead of a B-shape. In this manner, the surgical staple, when fired from staple pusher member 22 and formed against anvil member 26, would be able to straddle the distal tip of dispensing device "D" and thereby better maintain the distal tip in a straight line during withdrawal of the distal tip from between the layers of tissue "T".

It is envisioned and within the scope of the present disclosure, that the process of placing a tip of a needle between a pair of layers of tissue which are to joined to one another and then withdrawing the tip of the needle while simultaneously dispensing wound treatment material between the layers of tissue, following the approximation of the layers of tissue to one another, may be used in conjunction with annular and/or linear type surgical stapling apparatus or instruments.

It is contemplated that the wound treatment material "W" is any material for joining, healing, sealing or otherwise treating tissue. In a preferred embodiment, the wound treatment material is a bio-compatible sealant, including, and not limited, to sealants which cure upon tissue contact, sealants which cure upon exposure to ultraviolet (UV) light, sealants which are two-part systems which are kept isolated from one another and are combined or any combinations thereof. Any known suitable adhesive may be used. In one embodiment, it is contemplated that such sealants and/or adhesives are curable. For example, sealants may have a cure time of from about 10 to 15 seconds may be used. In preferred embodiments, the sealant and/or adhesive is a bioabsorbable and/or bio-resorbable material. In another embodiment, it is contemplated that a sealant and/or adhesive having a cure time of about 30 seconds may be used. It is further envisioned that wound treatment material "W" may be a pre-cured adhesive or sealant. The pre-cured adhesive or sealant may react with the moisture and/or heat of the body tissue to thereby activate the sealing and/or adhesive properties of the sealant or adhesive.

In certain preferred embodiments, the wound treatment material comprises a sealant. Such a sealant is desirably a PEG-based material. Examples of classes of materials useful as the sealant and/or adhesive include acrylate or methacrylate functional hydrogels in the presence of a biocompatible photoinitiator, alkyl-cyanoacrylates, isocyanate functional macromers with or without amine functional macromers, succinimidyl ester functional macromers with amine or sulfhydryl functional macromers, epoxy functional macromers with amine functional macromers, mixtures of proteins or polypeptides in the presence of aldehyde crosslinkers, Genipin, or water-soluble carbodiimides, anionic polysaccharides in the presence of polyvalent cations, etc.

Some specific materials which may be utilized include isocyanate terminated hydrophilic urethane prepolymers derived from organic polyisocyanates and oxyethylene-based diols or polyols, including those disclosed in U.S. Pat. Nos. 6,702,731 and 6,296,607 and U.S. Published Patent Application No. 2004/0068078; alpha-cyanoacrylate based adhesives including those disclosed in U.S. Pat. No. 6,565,840; alkyl ester based cyanoacrylate adhesives including those disclosed in U.S. Pat. No. 6,620,846; adhesives based on biocompatible cross-linked polymers formed from water soluble precursors having electrophilic and nucleophilic groups capable of reacting and cross-linking in situ, including those disclosed in U.S. Pat. No. 6,566,406; two part adhesive systems including those based upon polyalkylene oxide backbones substituted with one or more isocyanate groups in combination with bioabsorbable diamine compounds, or polyalkylene oxide backbones substituted with one or more amine groups in combination with bioabsorbable diisoycanate compounds as disclosed in U.S. Published Patent Application No. 2003/0032734, the contents of which are incorporated by reference herein; and isocyanate terminated hydrophilic urethane prepolymers derived from aromatic diisocyanates and polyols as disclosed in U.S. Published Patent Application No. 2004/0115229, the contents of which are incorporated by reference herein.

It is envisioned and within the scope of the present disclosure that wound treatment material "W" may include one or a combination of adhesives, hemostats, sealants, or any other tissue or wound-treating material. Surgical biocompatible wound treatment materials "W", which may be used in accordance with the present disclosure, include adhesives whose function is to attach or hold organs, tissues or structures, sealants to prevent fluid leakage, and hemostats to halt or prevent bleeding. Examples of adhesives which can be employed include protein derived, aldehyde-based adhesive materials, for example, the commercially available albumin/ glutaraldehyde materials sold under the trade designation BioGlue™ by Cryolife, Inc., and cyanoacrylate-based materials sold under the trade designations Indermil™ and Derma Bond™ by Tyco Healthcare Group, LP and Ethicon Endo-surgery, Inc., respectively. Examples of sealants, which can be employed, include fibrin sealants and collagen-based and synthetic polymer-based tissue sealants. Examples of commercially available sealants are synthetic polyethylene glycol-based, hydrogel materials sold under the trade designation CoSeal™ by Cohesion Technologies and Baxter International, Inc. Examples of hemostat materials, which can be employed, include fibrin-based, collagen-based, oxidized regenerated cellulose-based and gelatin-based topical hemostats. Examples of commercially available hemostat materials are fibrinogen-thrombin combination materials sold under the trade designations CoStasis™ by Tyco Healthcare Group, LP, and Tisseel™ sold by Baxter International, Inc. Hemostats herein include astringents, e.g., aluminum sulfate, and coagulants.

The medicament may include one or more medically and/ or surgically useful substances such as drugs, enzymes, growth factors, peptides, proteins, dyes, diagnostic agents or hemostasis agents, monoclonal antibodies, or any other pharmaceutical used in the prevention of stenosis.

Wound treatment material "W" may include visco-elastic film forming materials, cross-linking reactive agents, and energy curable adhesives. It is envisioned that wound treatment material "W", and in particular, adhesive may be cured with the application of water and/or glycerin thereto. In this manner, the water and/or glycerin cure the adhesive and hydrate the wound.

It is further contemplated that wound treatment material "W" may include, for example, compositions and/or compounds which accelerate or beneficially modify the healing process when particles of the composition and/or compound are applied to or exposed to a surgical repair site. For example, the wound treatment material "W" may be a therapeutic agent which will be deposited at the repair site. The therapeutic agent can be chosen for its antimicrobial properties, capability for promoting repair or reconstruction and/or new tissue growth. Antimicrobial agents such as broad spectrum antibiotic (gentamycin sulfate, erythromycin or derivatized glycopeptides) which are slowly released into the tissue can be applied in this manner to aid in combating clinical and sub-clinical infections in a tissue repair site. To promote repair and/or tissue growth, wound treatment material "W" may include one or several growth promoting factors, e.g., fibroblast growth factor, bone growth factor, epidermal growth factor, platelet derived growth factor, macrophage derived growth factor, alveolar derived growth factor, monocyte derived growth factor, magainin, and so forth. Some therapeutic indications are: glycerol with tissue or kidney plasminogen activator to cause thrombosis, superoxide dimutase to scavenge tissue damaging free radicals, tumor necrosis factor for cancer therapy or colony stimulating factor and interferon, interleukin-2 or other lymphokine to enhance the immune system.

It will be understood that various modifications may be made to the embodiments of the presently disclosed surgical stapling apparatus and the various dispensing systems and methods described above. Therefore, the above description should not be construed as limiting, but merely as exemplifications of preferred embodiments. Those skilled in the art will envision other modifications within the scope and spirit of the present disclosure.

What is claimed is:

1. A surgical stapling apparatus, comprising:
 a body portion;
 an actuation assembly operatively supported at a proximal end of the body portion;
 a staple pusher member operatively disposed at a distal end of the body portion and being operatively connected to the actuation assembly for expelling staples from the body portion;
 an anvil assembly movably mounted at the distal end of the body portion for movement toward and away from the staple pusher member;
 an approximation assembly extending between the body portion and the anvil assembly for moving the anvil assembly toward and away from the body portion; and
 a wound treatment material dispersion system for delivering wound treatment material to a target surgical site, the dispersion system including:
 at least one port formed in the anvil assembly oriented to dispense wound treatment material in an outward direction; and
 an ampoule containing a wound treatment material and being configured for selective disposition within the anvil assembly and for selective fluid communication with each of the at least one port.

2. The surgical stapling apparatus according to claim 1, wherein the wound treatment material is at least one of an adhesive, a sealant, a hemostat, and a medicament.

3. The surgical stapling apparatus according to claim 1, wherein the anvil assembly comprises a hollow tubular stem including an open proximal end, the hollow tubular stem configured to receive the ampoule containing the wound treatment material.

4. The surgical stapling apparatus of claim 3, wherein the anvil assembly further comprises a cap selectively operatively connectable to the proximal end of the stem.

5. The surgical stapling apparatus according to claim 3, wherein the dispersion system includes a piston configured and dimensioned for insertion into the hollow tubular stem of the anvil assembly to engage the ampoule upon approximation of the anvil assembly and the body portion, the ampoule is compressed and wound treatment material is forced out through the port of the anvil assembly and onto a target surgical site at least one of before, during and after firing of the surgical stapling apparatus.

6. The surgical stapling apparatus of claim 1, wherein the ampoule is constructed from a breakable material, and wherein, during use, upon approximation of the anvil assembly and the body portion, the ampoule is compressed and wound treatment material is delivered from the ampoule to the at least one port of the anvil assembly.

7. The surgical stapling apparatus according to claim 1, wherein the dispersion system further includes at least one drape supported on and substantially surrounding a stem of the anvil assembly, wherein the drape includes an undeployed condition in which the drape is in relatively close proximity to the stem of the anvil assembly, and a deployed condition in which the drape is in relatively spaced relation to the stem of the anvil assembly.

8. The surgical stapling apparatus according to claim 7, wherein the dispersion system includes a first drape positioned distally of the port of the anvil assembly and a second drape positioned proximally of the port of the anvil assembly.

9. The surgical stapling apparatus according to claim 8, wherein, when the drapes are in the deployable condition, the drapes direct the dispersion of the wound treatment material.

10. The surgical stapling apparatus according to claim 1, wherein a stem of the anvil assembly includes a first annular groove formed distally of the port of the anvil assembly and a second annular groove formed proximally of the port of the anvil assembly.

11. The surgical stapling apparatus according to claim 1, further comprising an annular blade retractably disposed at a distal end of the body portion, wherein the annular blade includes a plurality of openings formed therein.

12. The surgical stapling apparatus according to claim 1, further comprising a splash guard including a central hub defining a lumen therethrough for receiving a stem of the anvil assembly and an annular cuff supported on the central hub and extending at least substantially therearound, wherein the annular cuff is disposed radially outward of a staple line of the surgical stapling apparatus.

13. The surgical stapling apparatus according to claim 12, wherein the splash guard further comprises at least one spoke interconnecting the annular cuff to the central hub.

14. The surgical stapling apparatus according to claim 13, wherein the annular cuff of the splash guard is concave and defines an upper rim and a lower rim, wherein the upper and lower rims are dimensioned to contact an outer surface of the target surgical site.

15. A kit for performing a surgical anastomotic procedure, the kit comprising:
- a surgical stapling apparatus including:
  - a body portion;
  - an actuation assembly operatively supported at a proximal end of the body portion;
  - a staple pusher member operatively disposed at a distal end of the body portion and being operatively connected to the actuation assembly for expelling staples from the body portion;
  - an anvil assembly movably mounted at the distal end of the body portion for movement toward and away from the staple pusher member, the anvil assembly including a stem defining a cavity and having an open proximal end, and at least one port formed in a surface of the stem; and
  - an approximation assembly extending between the body portion and the anvil assembly for moving the anvil assembly toward and away from the body portion;
- at least one ampoule containing a wound treatment material, the ampoule configured to be positioned within the cavity of the stem of the anvil assembly and for selective fluid communication with each of the at least one port; and
- a splash guard including a central hub defining a lumen therethrough for receiving the stem of the anvil assembly and an annular cuff supported on the central hub and extending at least substantially therearound.

16. The kit according to claim 15, further comprising a cap operatively connectable to the open proximal end of the stem of the anvil assembly.

17. The kit according to claim 15, further comprising a plunger configured for selective slidable engagement with the open proximal end and the cavity of the stem of the anvil assembly.

\* \* \* \* \*